(12) United States Patent
Petit et al.

(10) Patent No.: US 7,879,101 B2
(45) Date of Patent: Feb. 1, 2011

(54) INTERVERTEBRAL PROSTHESIS

(75) Inventors: Dominique Petit, Verton (FR); Thomas Droulout, Cachan (FR); Vincent Sene, Cachan (FR)

(73) Assignee: Spinevision, Paris (FR)

( * ) Notice: Subject to any disclaimer, the term of this patent is extended or adjusted under 35 U.S.C. 154(b) by 0 days.

(21) Appl. No.: 10/545,450

(22) PCT Filed: Feb. 13, 2004

(86) PCT No.: PCT/FR2004/000341

§ 371 (c)(1),
(2), (4) Date: Dec. 14, 2005

(87) PCT Pub. No.: WO2004/073561

PCT Pub. Date: Sep. 2, 2004

(65) Prior Publication Data

US 2006/0235524 A1 Oct. 19, 2006

(30) Foreign Application Priority Data

Feb. 13, 2003 (FR) .................................. 03 01753

(51) Int. Cl.
*A61F 2/44* (2006.01)
(52) U.S. Cl. .................................................. 623/17.15
(58) Field of Classification Search .... 623/17.11–17.16
See application file for complete search history.

(56) References Cited

U.S. PATENT DOCUMENTS

| | | | | |
|---|---|---|---|---|
| 4,863,477 A | * | 9/1989 | Monson | 623/17.12 |
| 4,932,975 A | * | 6/1990 | Main et al. | 623/17.12 |
| 4,946,378 A | * | 8/1990 | Hirayama et al. | 623/17.16 |
| 5,314,477 A | * | 5/1994 | Marnay | 623/17.15 |
| 5,375,823 A | * | 12/1994 | Navas | 623/17.15 |
| 5,507,816 A | * | 4/1996 | Bullivant | 623/17.15 |
| 5,674,294 A | * | 10/1997 | Bainville et al. | 623/17.16 |
| 5,989,291 A | * | 11/1999 | Ralph et al. | 623/17.15 |
| 6,126,689 A | * | 10/2000 | Brett | 623/17.16 |
| 6,156,067 A | * | 12/2000 | Bryan et al. | 623/17.15 |
| 6,375,682 B1 | * | 4/2002 | Fleischmann et al. | 623/17.12 |
| 6,454,806 B1 | * | 9/2002 | Cohen et al. | 623/17.15 |
| 6,468,310 B1 | * | 10/2002 | Ralph et al. | 623/17.13 |
| 6,533,817 B1 | * | 3/2003 | Norton et al. | 623/17.16 |
| 6,579,320 B1 | * | 6/2003 | Gauchet et al. | 623/17.15 |
| 6,579,321 B1 | * | 6/2003 | Gordon et al. | 623/17.16 |
| 6,863,689 B2 | * | 3/2005 | Ralph et al. | 623/17.16 |
| 2003/0191534 A1 | * | 10/2003 | Viart et al. | 623/17.15 |
| 2003/0233146 A1 | * | 12/2003 | Grinberg et al. | 623/17.14 |
| 2004/0034423 A1 | * | 2/2004 | Lyons et al. | 623/17.13 |
| 2004/0093082 A1 | * | 5/2004 | Ferree | 623/17.11 |
| 2004/0133278 A1 | * | 7/2004 | Marino et al. | 623/17.14 |
| 2004/0143332 A1 | * | 7/2004 | Krueger et al. | 623/17.14 |

FOREIGN PATENT DOCUMENTS

| | | |
|---|---|---|
| DE | 239 523 A1 | 10/1986 |
| WO | WO 01/68003 A1 | 9/2001 |

* cited by examiner

*Primary Examiner*—William H Matthews
*Assistant Examiner*—Ann Schillinger
(74) *Attorney, Agent, or Firm*—Bachman & LaPointe, P.C.

(57) ABSTRACT

An intervertebral prosthesis includes at least one core which is positioned between an upper plate and a lower plate, the prosthesis also includes an outer casing. The aforementioned plates comprise respective inner faces which enable the core to move inside the prosthesis.

29 Claims, 20 Drawing Sheets

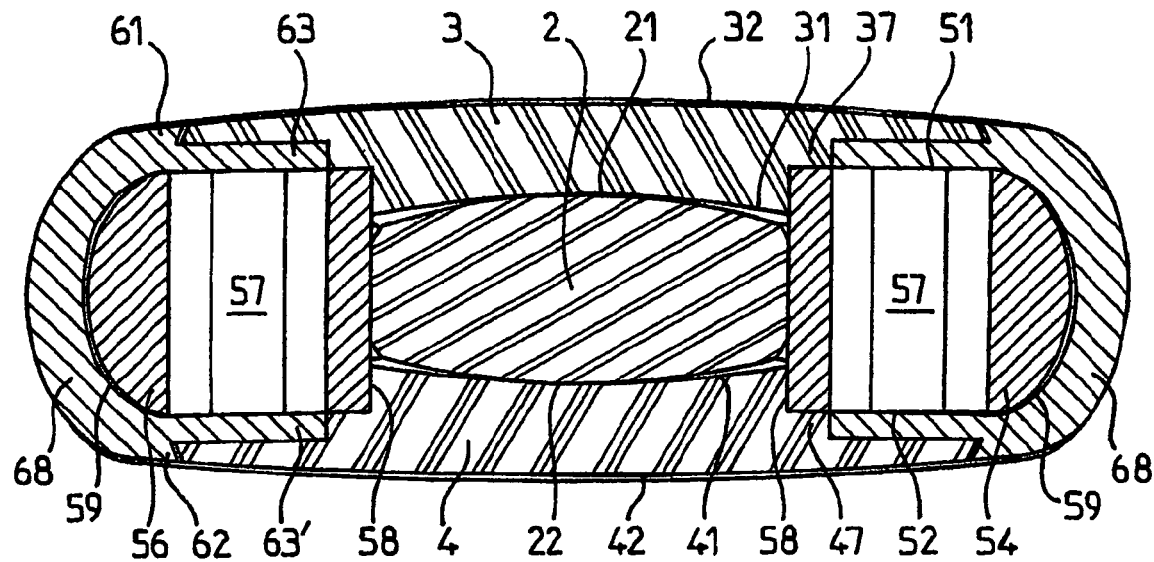
FIG.3  A-A
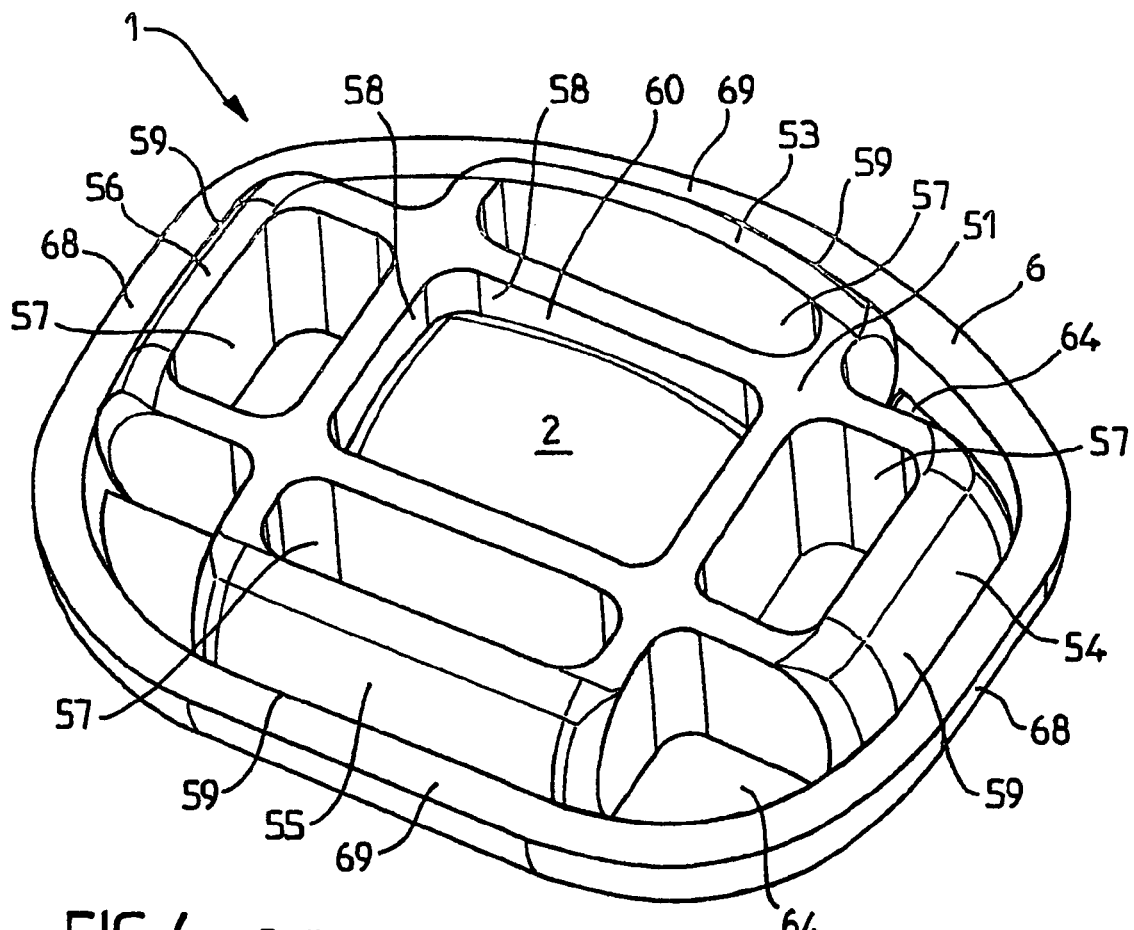
FIG.4  B-B

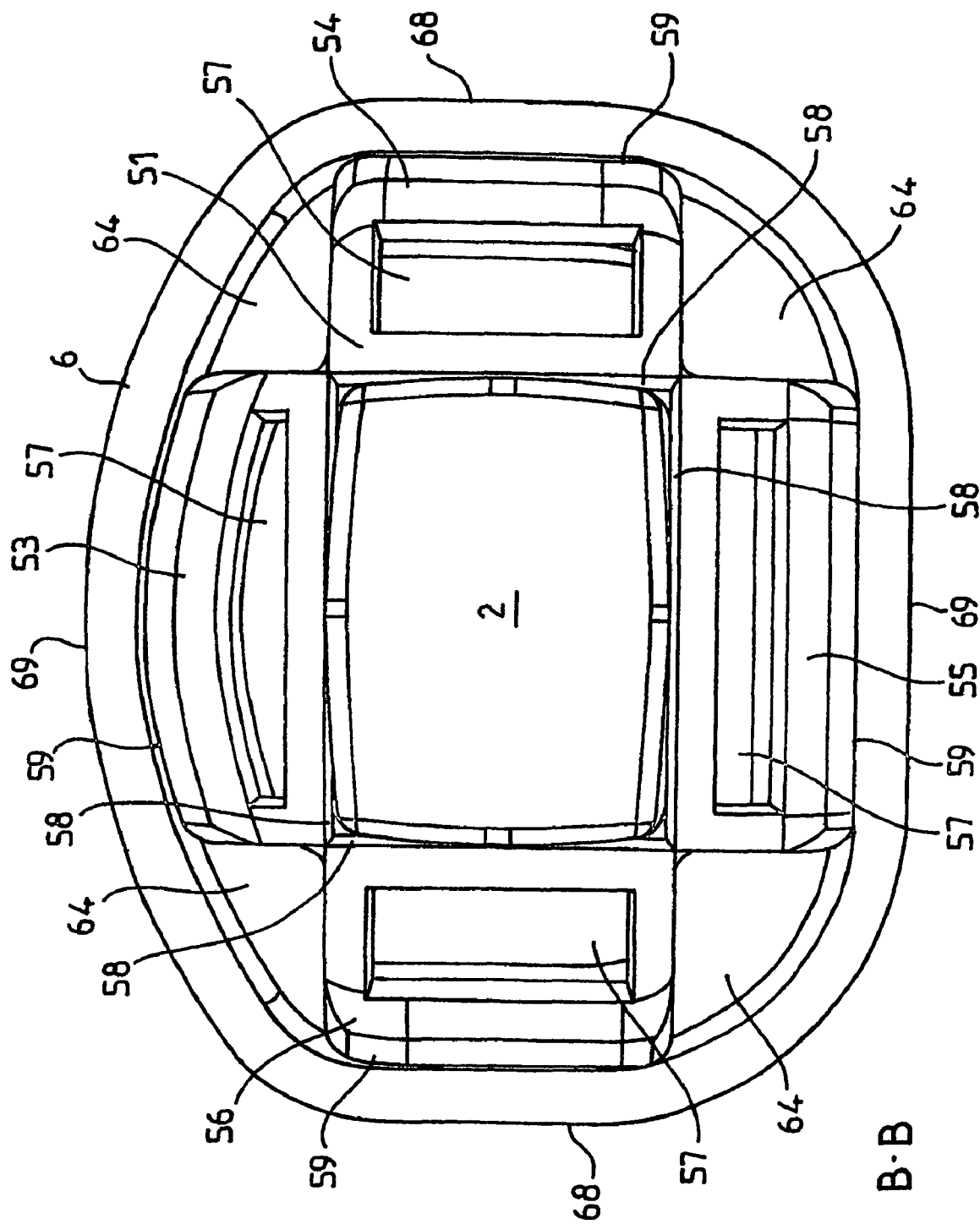
FIG.5 B-B

INTERVERTEBRAL PROSTHESIS

BACKGROUND OF THE INVENTION (1) Field of the Invention

The present invention relates to the field of intervertebral disk prostheses.

The present invention relates more particularly to an intervertebral prosthesis of the type formed at least of one core which is positioned between an upper plate and a lower plate, said prosthesis furthermore comprising at least one outer casing.

(2) Prior Art

Intervertebral prostheses of this type are already known from the prior art.

There is thus proposed in U.S. Pat. No. 5,674,296 a vertebral disk endoprosthesis comprising a core, preferably an elastic core, and rigid elements with concave inner surfaces which at least partly surround the core. The endoprosthesis also comprises a sealing element which is formed of flexible material and is fixed to the rigid elements and surrounds the core.

This vertebral disk endoprosthesis (18) comprises a flexible core (20, 24), rigid concave/convex plates (30, 32, 34) arranged above and below the core, a relatively rigid peripheral packing ring (22) which surrounds the core (20, 24), and a sealing member (110) made of a flexible material which is attached to the concave/convex plates and surrounds the core and the packing ring.

Each concave/convex plate has a relatively constant thickness in cross section and has on the one hand a convex outer surface for engaging in the adjacent bone structure which has previously been drilled and on the other hand a corresponding concave inner surface for holding the resilient body of the core.

In this prosthesis, the shape of the inner faces of the plates is identical to the shape of the adjacent core and the core is thus strictly immobile.

The prostheses of the prior art are not satisfactory since they do not make it possible to guide and cushion the displacements of the underlying and overlying vertebrae in the same way as anatomical disks.

SUMMARY OF THE INVENTION

The present invention aims to overcome the drawbacks of the prior art by proposing a prosthesis which simultaneously guides and cushions the forward/backward flexion/extension and left/right inclination movements of the underlying and overlying vertebrae.

To this end, the present invention is of the type described above and it is noteworthy, in its widest sense, in that said plates respectively comprise inner faces which permit a movement of the core inside said prosthesis.

Said core is preferably surrounded laterally by a flexible inner casing, said inner casing having favored directions of flexibility, these preferably being two in number and being oriented perpendicularly.

Said outer casing is preferably flexible.

Preferably at least one inner face respectively of said upper plate and/or lower plate, and even more preferably the two inner faces of the plates, has/have means for guiding the displacement of said core.

Said guiding means are preferably oriented in two perpendicular directions and preferably in the same directions as the favored directions of flexibility of the inner casing.

Said guiding means preferably consist of inclined surfaces, whose outer edges are oriented toward the core.

In one variant, at least one inner face respectively of said upper plate and/or lower plate preferably has a projection and said core furthermore preferably comprises, respectively on its upper face and/or lower face, two grooves which are oriented in two perpendicular directions.

In this variant, said grooves are preferably oriented in the same directions as the favored directions of flexibility of the inner casing.

In one variant, at least one inner face respectively of said upper plate and/or lower plate, and preferably the two inner faces of the plates, is/are flat.

Said core preferably has a substantially parallelepiped shape.

The upper face and lower face of said core are preferably rounded in the favored directions of flexibility of the inner casing.

Said core preferably has rounded edges.

Said inner casing preferably has in horizontal section the shape of a cross formed by four horizontal arms which are oriented perpendicularly.

Said arms preferably each have a hole which opens onto the upper face and lower face of said inner casing.

The centripetal faces of said arms are preferably straight and the centrifugal faces of said arms are preferably rounded.

Said outer casing preferably has inner fins which are designed to hold the horizontal arms of the inner casing, at the corner between the arms of the cross shape.

In one variant, the inner casing and the outer casing are made in one piece.

Said outer casing preferably has cutouts on its upper wall and/or lower wall for the passage of the outer faces respectively of the upper plate and lower plate.

In another variant, said upper plate and/or lower plate has/have an annular cavity adjacent to the outer face and said upper wall and/or lower wall respectively has/have a centripetal flange which is designed to cooperate with said annular cavity.

In another variant, said upper plate and/or lower plate is/are flexible.

In another variant, said upper plate and/or lower plate has/have a fixing rail on its/their outer face(s).

The prosthesis preferably furthermore comprises fixing means for fixing respectively the upper plate and/or lower plate.

In one advantageous embodiment of the invention, the intervertebral prosthesis comprises two cores.

Preferably, the inner casing has a longitudinal median membrane which separates the cores.

Advantageously, the membrane of said inner casing is flexible.

Advantageously, at least one of the plates comprises a through-hole to allow the passage of a fluid into said inner casing.

Advantageously, the through-hole is extended by a threaded tubular zone which is designed to cooperate with a complementary threaded zone of a contact element which is designed to be brought into contact with one of the vertebrae.

Advantageously, said prosthesis formed of said core(s), the inner casing, the outer casing and the plates is overmolded with a flexible elastomer.

Advantageously, said core(s) is/are solid or liquid.

Advantageously, the present invention makes it possible to restore the natural movements of the underlying and overlying vertebrae or, if necessary, to limit certain movement capabilities in one direction or another.

Also advantageously, it is possible to select constituent materials as a function of the increasing resistances to movement which are desired and as a function of the favored directions of flexibility which are desired for each of the parts:
the upper plate and/or lower plate, and/or
the core, and/or
the inner casing, and/or
the outer casing.

Also advantageously, the present invention permits good shock absorption.

It also makes it possible to preserve the articular surfaces.
It exhibits high reliability over time.
It is furthermore simple to install.

BRIEF DESCRIPTION OF THE DRAWINGS

The invention will be better understood with the aid of the following description of one embodiment of the invention, said description being given solely by way of example and with reference to the appended figures:

FIG. 3 shows a view in vertical section along AA of FIG. 1;

FIG. 4 shows a perspective view of the partial horizontal section along BB of FIG. 1;

FIG. 5 shows a view from above of the partial horizontal section along BB of FIG. 1;

DETAILED DESCRIPTION OF THE PREFERRED EMBODIMENT(S)

Figure 1:
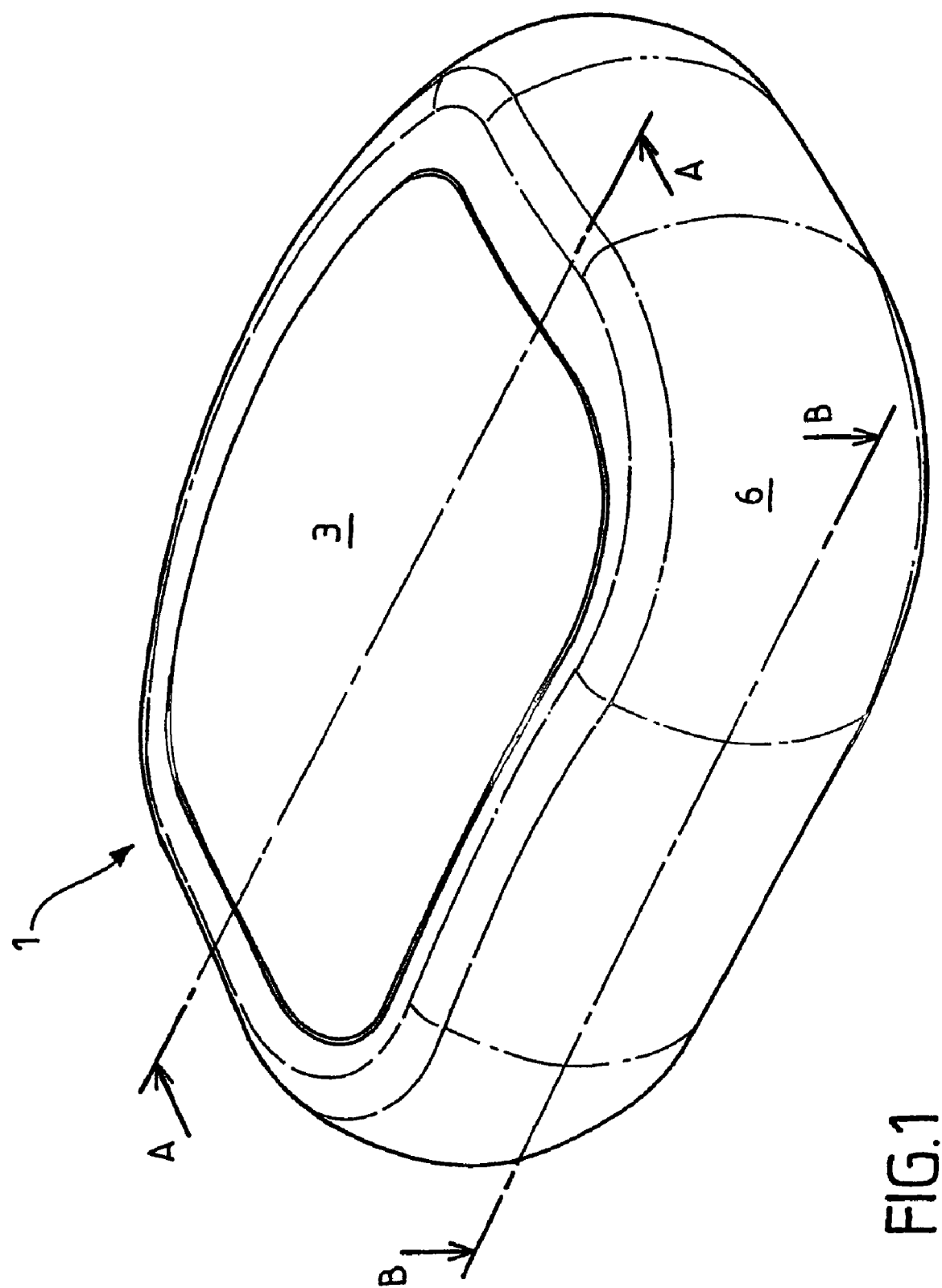
FIG. 1 shows a perspective view of the basic version of the prosthesis according to the invention.

The prosthesis according to the present invention, which is shown in its basic version in FIG. 1, is an intervertebral prosthesis (1) of the type formed at least of one core (2) which is positioned between an upper plate (3) and a lower plate (4).

In this basic version, the plates (3, 4) are rigid.

This prosthesis is designed to be positioned between two vertebrae, in place of a disk, when the latter is failing and causes pain.

The upper plate (3) and lower plate (4) respectively have an inner face (31, 41).

The upper plate (3) has an outer face (32) which is designed to cooperate with the lower face of the vertebra located above the prosthesis, and the lower plate (4) has an outer face (42) which is designed to cooperate with the upper face of the vertebra located below the prosthesis. The outer faces (32, 42) are essentially horizontal.

The aim of the prosthesis according to the invention is to completely replace the painful disk and to once again allow the movements of the vertebrae located thereabove and therebelow with respect to one another, as if the disk had not failed.

In order to allow these movements of the vertebrae, said core (2) can move inside the prosthesis, between the inner faces (31, 41) of the plates (3, 4).

The mobility of the core (2) is essentially horizontal and gives rise to a change in the center of gravity of the prosthesis.

The shape of the inner faces (31, 41) is complementary to the shape of the adjacent core, without being completely identical, so as to allow the displacement of the core (2) with respect to the plates.

The core (2) is surrounded laterally by an inner casing (5). This inner casing (5) is flexible and has favored directions of flexibility. Said prosthesis (1) furthermore comprises an outer casing (6) which is also flexible.

This outer casing (6) contains the inner casing (5), which itself contains the core (2), as can be seen in FIGS. 2 to 5.

Said inner casing (5) has two favored directions of flexibility which are oriented perpendicularly, so as to make it possible to restore on the one hand the left/right lateral inclination movements and on the other hand the flexion/extension movements, the rotational movements being restored in particular at the intersection of the two favored directions, respectively allowing the left/right inclinations and the flexion/extension movements.

The flexible elements of the prosthesis according to the invention may consist of elements made of biomaterial (polyurethane, polycarbonate, polyvinyl alcohol, etc.) and the rigid elements may consist of elements made of biomaterial or of metal or metal alloy.

Figure 6:
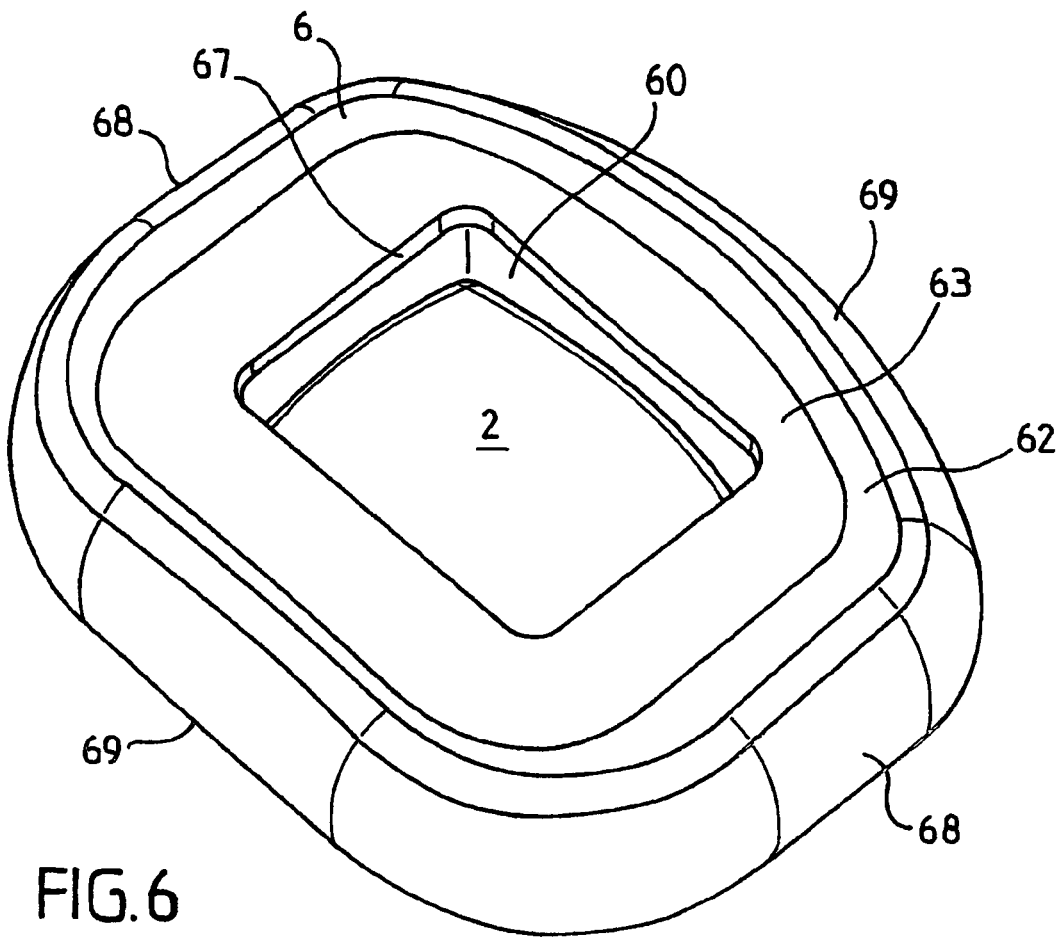
FIG. 6 shows a view from above of the basic version of the prosthesis according to the invention, without the upper plate.
Figure 7:
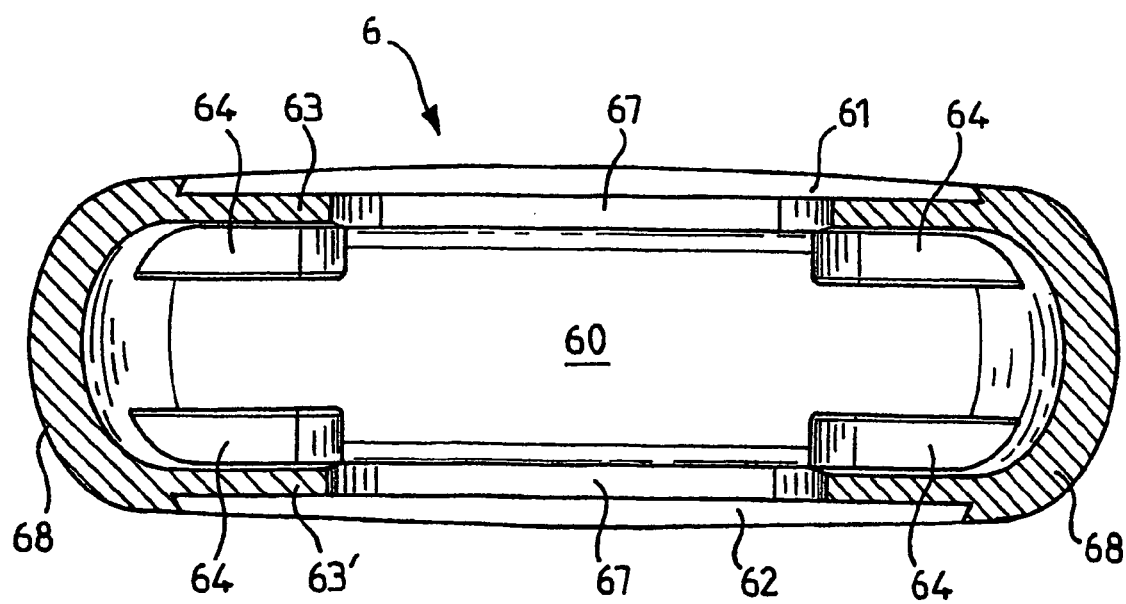
FIG. 7 shows a view in vertical section along AA of FIG. 1 of the outer casing of the basic version of the prosthesis according to the invention.

The outer casing (6) has a parallelepiped overall shape and comprises an upper wall (61), a lower wall (62), frontal side walls (68) and sagittal side walls (69). The frontal side walls (68) are substantially rounded in the form of a vertical arc of a circle, as can be seen in FIG. 3, whereas the sagittal side walls (69) are rounded both in the form of a horizontal arc of a circle and in the form of a vertical arc of a circle, as can be seen in FIGS. 5 to 7. The upper wall (61) and lower wall (62) are substantially flat.

The corners between the walls of the outer casing (6) are rounded with a small radius of curvature.

The outer casing (6) has an inner cavity (60) in the shape of a cross in horizontal section, as can be seen in FIG. 5, in which the inner casing (5) is positioned.

The outer casing (6) has a hole (67) on its upper wall (61) and lower wall (62), as can be seen in FIG. 6, for the passage of the outer faces (32, 42) respectively of the upper plate (3) and lower plate (4).

The frontal side walls (68) and sagittal side walls (69) have a substantially constant thickness.

Said upper wall (61) or lower wall (62), and preferably both the upper wall (61) and lower wall (62), has/have respectively a centripetal flange (63, 63') formed toward the inside, on which the outer face(s) (32, 42) of the upper plate (3) and/or lower plate (4) come(s) to rest, as can be seen in FIG. 3.

Said outer casing (6) has horizontal inner fins (64) which are positioned in the lower and upper part of the inner wall of the casing and are oriented toward the inside.

The inner cavity (60) therefore has both a cross shape in horizontal section and a cross shape in vertical section, as can be seen in FIG. 7.

The flexibility and suppleness of the outer casing (6) make it possible to hold all the elements forming the prosthesis and participate in vertical cushioning, that is to say the resistance to compression.

This flexibility and this suppleness of the outer casing (6) also make it possible to achieve cushioning and a return to the central position in the event of rotational movements, so as to limit these movements.

Figure 8:
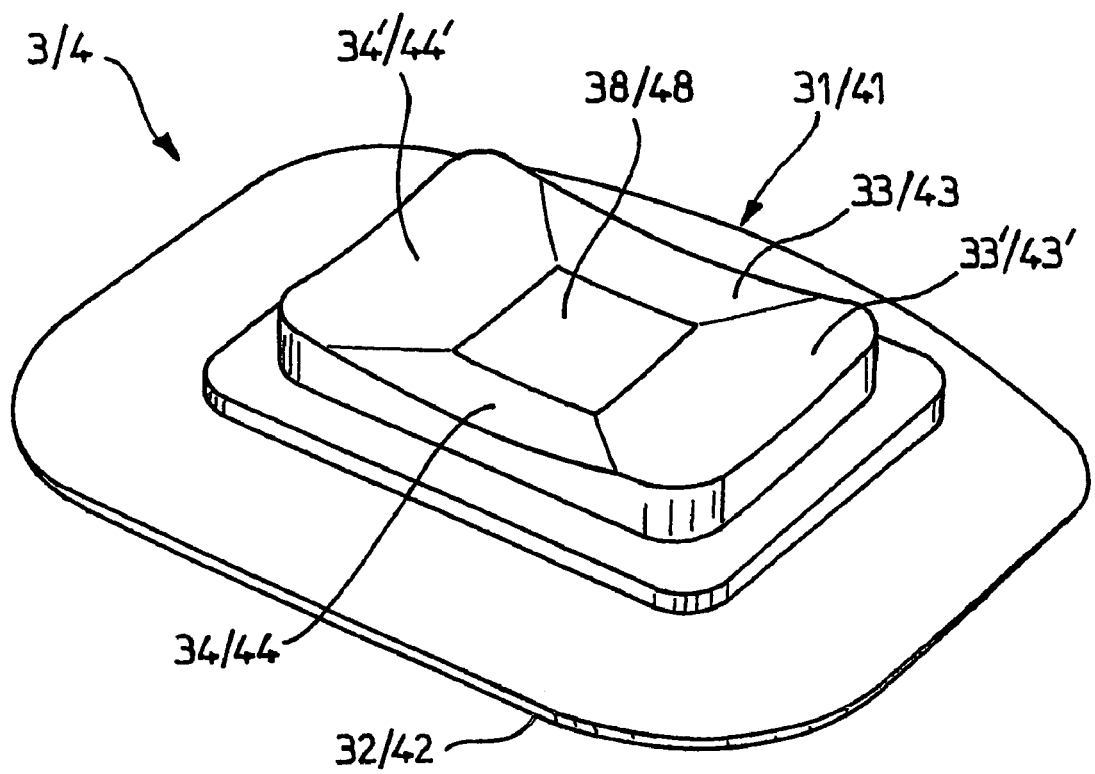
FIG. 8 shows a perspective view of a plate for the basic version of the prosthesis according to the invention.

As shown in FIG. 8, the two inner faces (31, 41) have means for guiding the displacement of said core (2), said guiding means being oriented in two perpendicular directions.

These guiding means are oriented in the same directions as the favored directions of flexibility of the inner casing (5).

Said guiding means consist, in respect of the upper plate (3), of inclined surfaces (33, 33', 34, 34'), the outer edges of which are lowered toward the core (2), that is to say downward, and of a horizontal bottom surface (38), and in respect of the lower plate (4) they consist of inclined surfaces (43, 43', 44, 44'), the outer edges of which are raised toward the core (2), that is to say upward, and of a horizontal bottom surface (48).

The upper plate (3) and lower plate (4) furthermore each comprise a horizontal rectangular flange (37, 47) which is located between the inner face (31, 41) and the outer face (32, 42), said flanges being of a size greater than the inner face (31, 41) and less than that of the outer face (32, 42). These flanges (37, 47) are designed to be inserted into the holes (67) made in the upper wall (61) and lower wall (62) of the outer casing (6).

In one variant of the basic version, one plate, and preferably both the upper plate (3) and lower plate (4), is/are flexible. This variant is advantageously associated with the variant of the invention with a rigid core.

In this variant with flexible plates, the flexibility of the plates promotes vertical cushioning and increases the ability of the plates to conform to the configuration of the adjacent bone walls.

Figure 2:
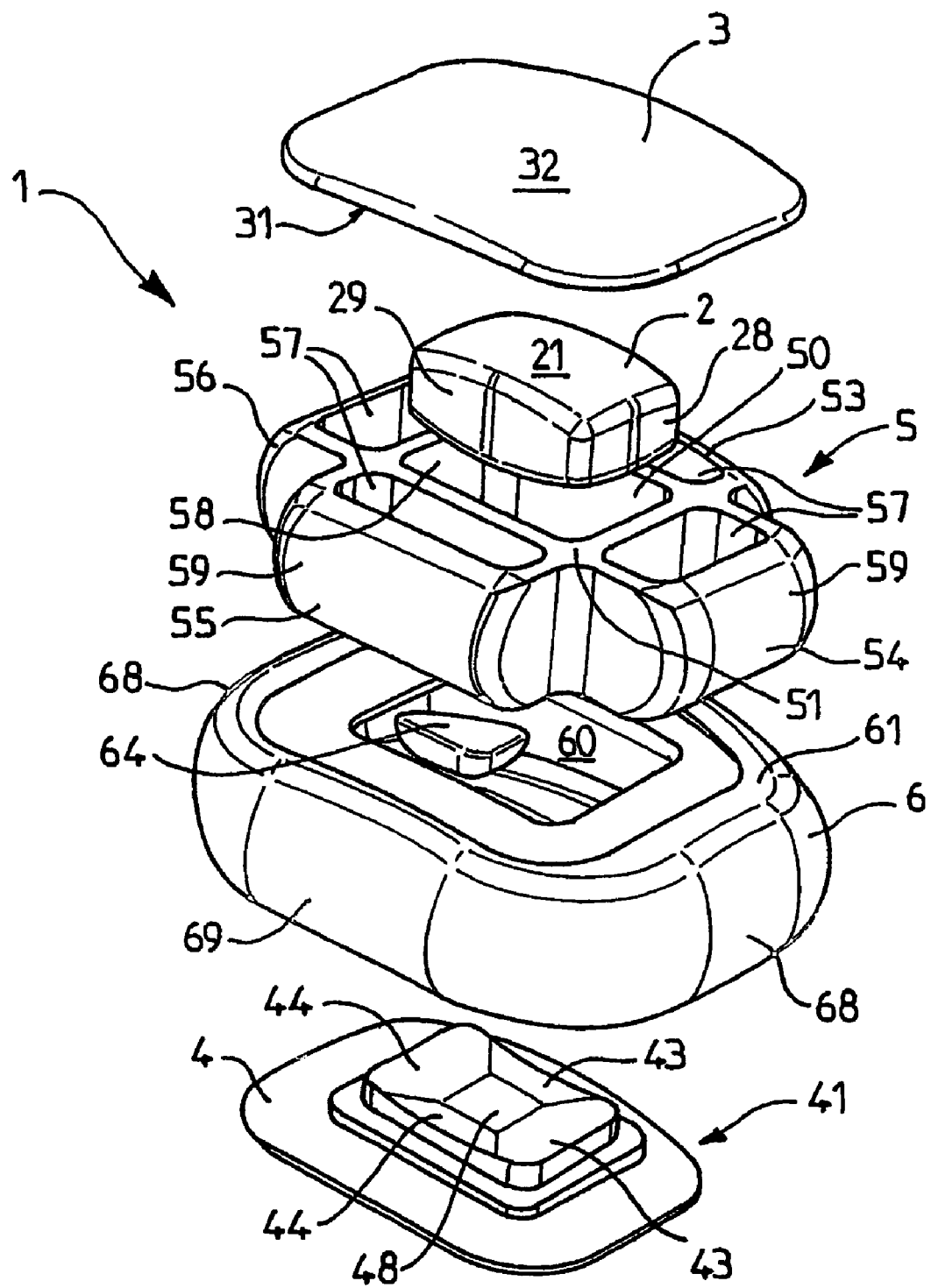
FIG. 2 shows an exploded view of the basic version of the prosthesis according to the invention.
Figure 9:
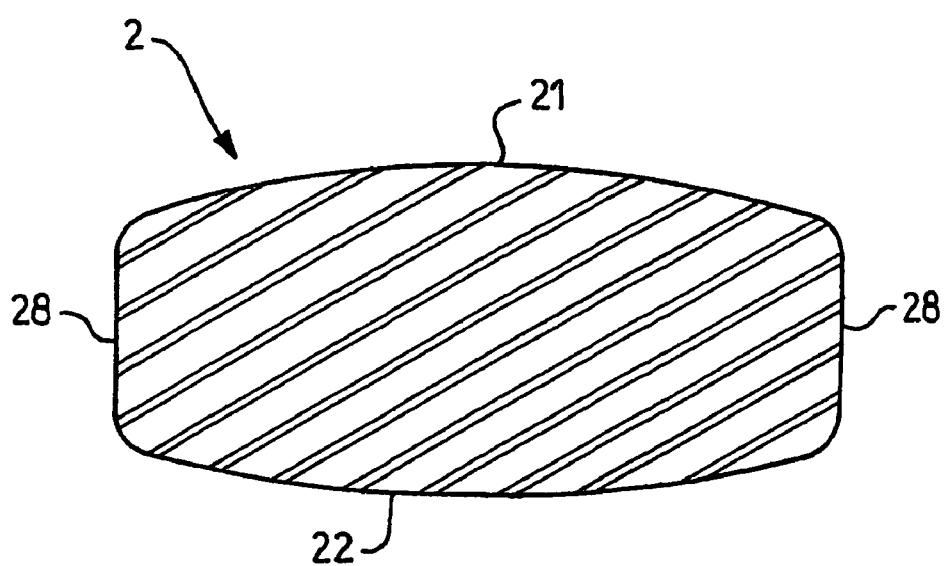
FIG. 9 shows a view in vertical section along AA of FIG. 1 of the core of the basic version of the prosthesis according to the invention.
Figure 10:
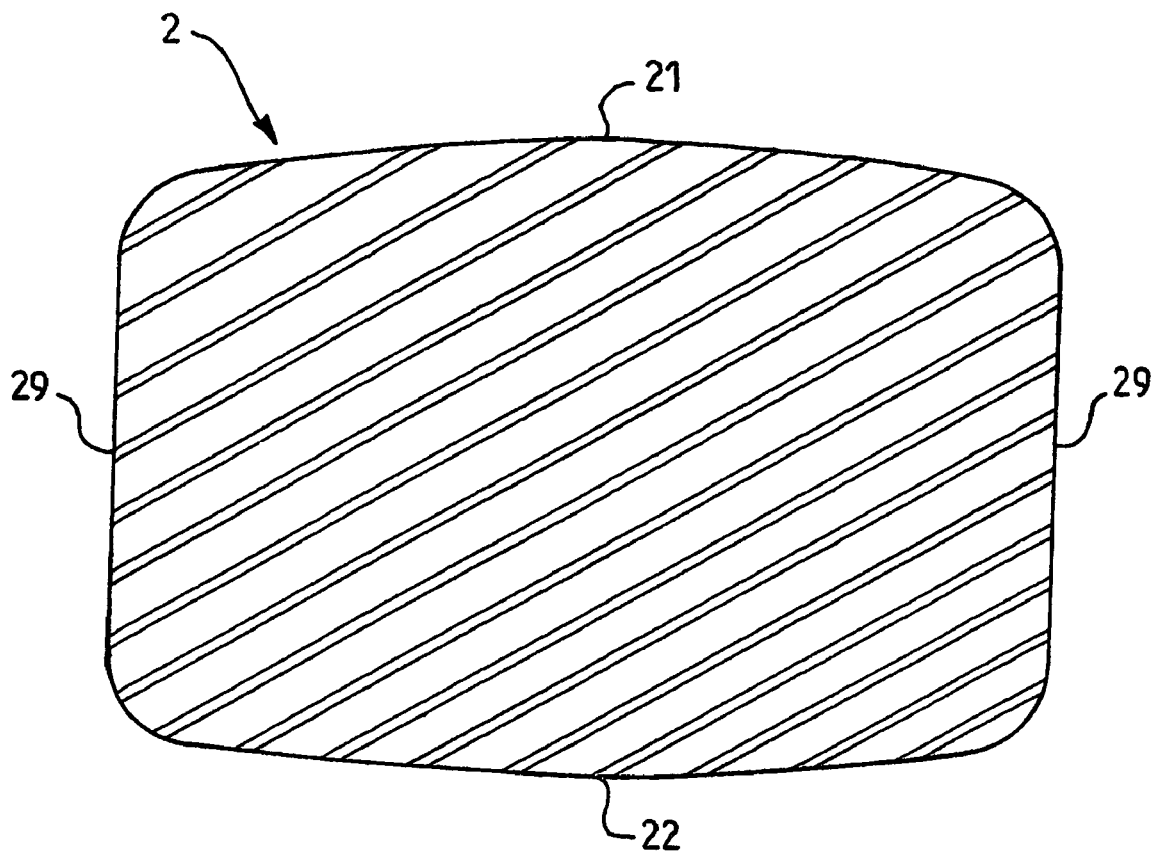
FIG. 10 shows a view in cross section of the core of the basic version of the prosthesis according to the invention.

The core (2) which is shown in FIGS. 9 and 10 has a substantially parallelepiped shape and comprises an upper wall (21), a lower wall (22) and frontal side walls (28) and sagittal side walls (29). The frontal side walls (28) and sagittal side walls (29) are essentially straight, as can be seen in FIGS. 2 and 9. The upper wall (21) and lower wall (22) are rounded in two perpendicular vertical arcs of a circle, as can be seen in the same figures.

The upper face (21) and lower face (22) of said core (2) are rounded in the favored directions of flexibility of the inner casing (5).

The corners or edges between the walls of the core (2) are rounded with a small radius of curvature.

The inner casing (5) has a central cavity (50) in which the core (2) is positioned.

In the basic version of the invention, said core (2) is rigid.

This cavity (50) has a straight parallelepiped shape so that, in the basic version, empty spaces are formed at the upper and lower frontal ends and at the upper and lower sagittal ends of this cavity, between the wall of this cavity and the outer wall of the core (2), as can be seen in FIG. 3.

The inner casing (5) has in horizontal section the shape of a cross formed by four horizontal arms (53, 54, 55, 56) which are oriented perpendicularly.

These arms (53, 54, 55, 56) extend in the favored directions of flexibility of the inner casing (5).

In the basic version of the invention, the arms (53, 54, 55, 56) form a whole, that is to say that the inner casing (5) forms a single part.

Figure 11:
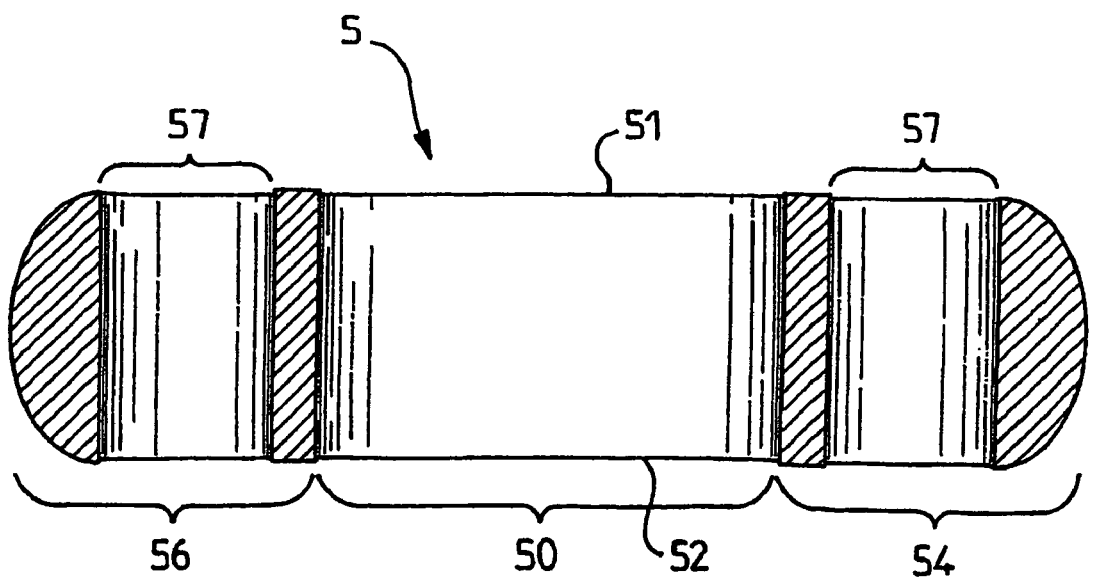
FIG. 11 shows a view in vertical section along AA of FIG. 1 of the inner casing of the basic version of the prosthesis according to the invention.

The arms (53, 54, 55, 56) each have a hole (57) which opens onto the upper face (51) and lower face (52) of said inner casing (5), as can be seen in FIGS. 4, 5 and 11, so as to increase the flexibility of the arms. These holes are empty or are filled with a fluid or with an elastic material.

The centripetal faces (58) of said arms (53, 54, 55, 56) which delimit the cavity (50) are straight.

The centrifugal faces (59) of said arms (53, 54, 55, 56) are rounded so as to be adapted to the inner faces of the frontal walls (68) and sagittal walls (69) of the outer casing (6).

The inner fins (64) of said outer casing (6) are thus designed to hold the horizontal arms (53, 54, 55, 56) of the inner casing (5), so as to create an additional rigidity in the directions which are not the favored directions of flexibility of the inner casing (5).

Figure 12:
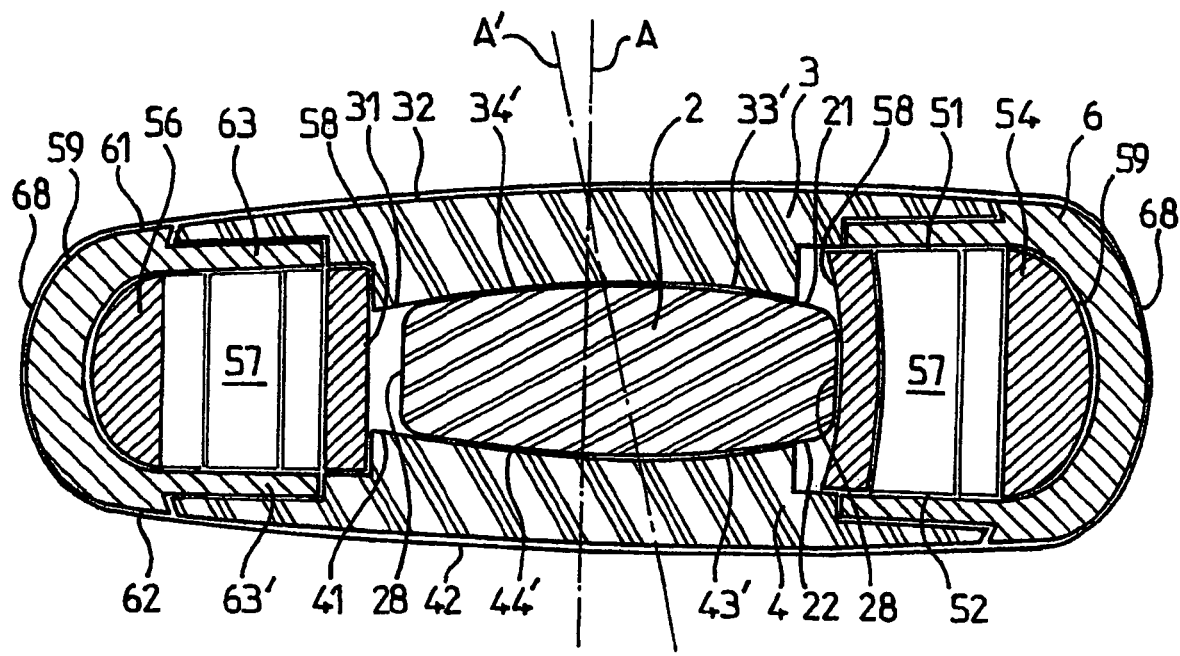
FIG. 12 shows a view in vertical section along AA of FIG. 1 of the basic version of the prosthesis according to the invention during a flexural movement.

The overall flexibility of the prosthesis in the basic version is considerable in the frontal and sagittal planes. This is because, during flexion of the spinal column, for example in the forward direction, as shown in FIG. 12, there is displacement of the core (2) in the inner casing (5) toward the rear of the cavity (50) and deformation of the rear centripetal face (58) of the inner casing (5). The mean axis of the column A at the prosthesis, which has passed from the vertical position to the forward-inclined position A', has undergone a rotation with respect to the vertical and a translation toward the rear. During this forward flexural movement, the upper face (21) of the core (2) slides on the inclined surfaces (33', 34') and the lower face (22) of the core (2) slides on the inclined surfaces (43', 44').

The centripetal face (58) of the arm (52) deforms so as to allow the displacement of the relatively rigid core (2) and offers an opposed resistance force which is a function of the flexibility of the material used for the inner casing (5). The greater the displacement of the core (2), the greater the force opposed to this displacement.

Figure 13:
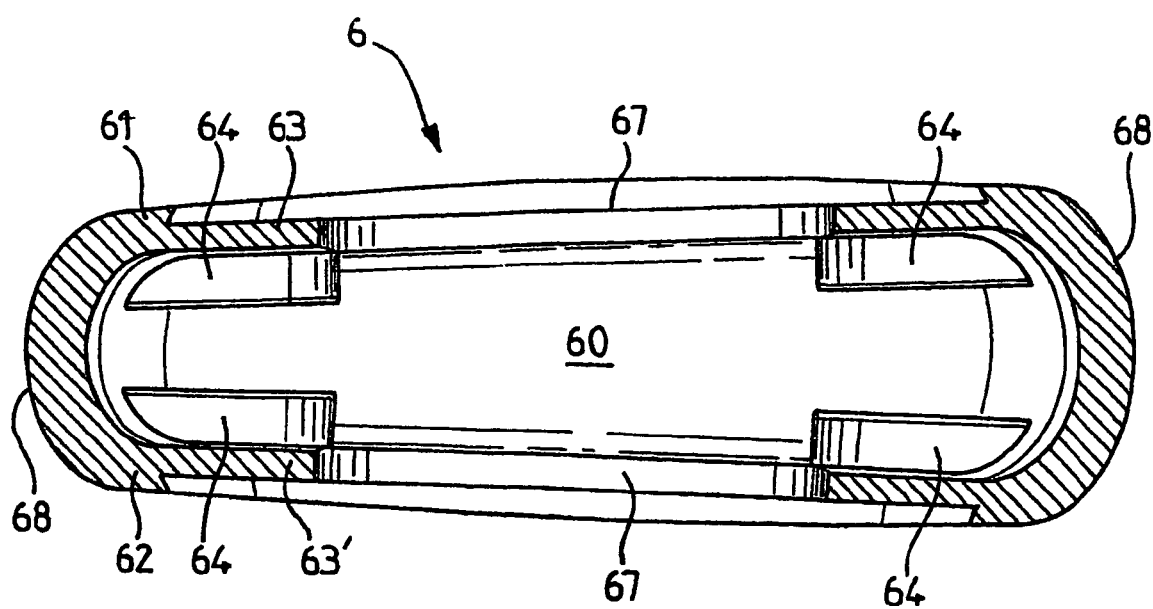
FIG. 13 shows the deformation of the outer casing during the movement shown in FIG. 12.

By virtue of the flexibility of the outer casing (6), the plates (3, 4) move away from one another at the rear of the prosthesis and move toward one another at the front, in the vertical direction. FIG. 13 shows the deformation of the outer casing (6) during this same movement of forward flexion.

Figure 14:
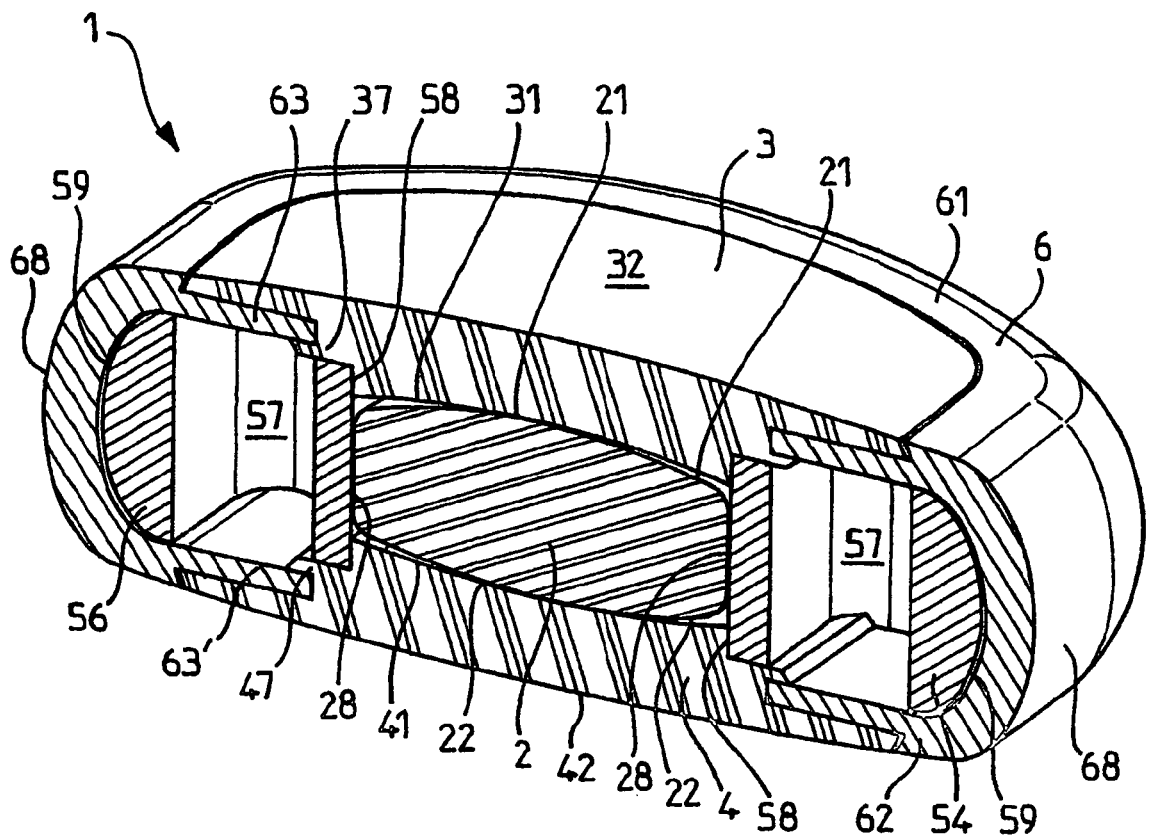
FIG. 14 shows a view in vertical section and in perspective of a variant of the invention in which the upper and lower plates are clipped into the outer casing.
Figure 15:
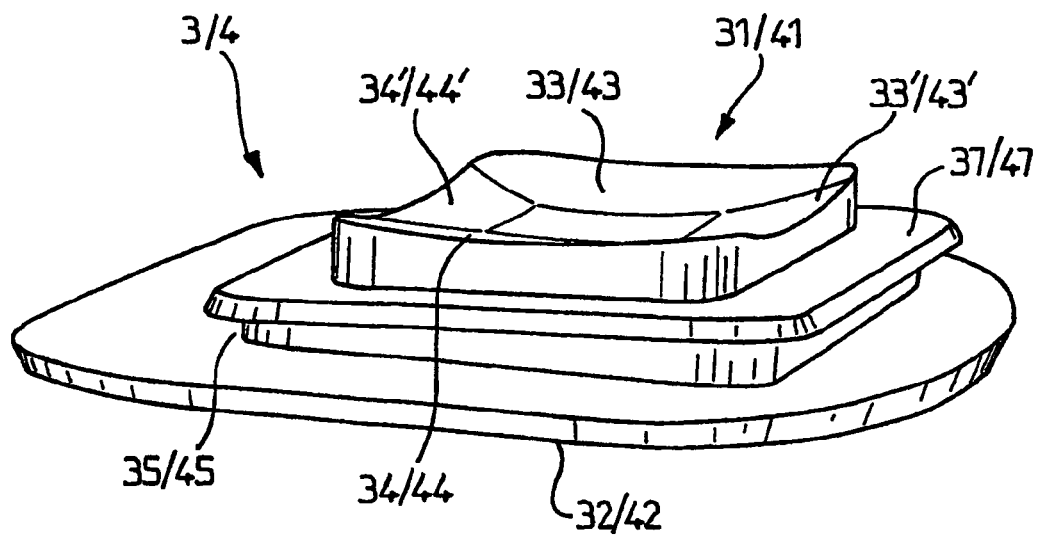
FIG. 15 shows a perspective view of a plate for the variant shown in FIG. 14.
Figure 16:
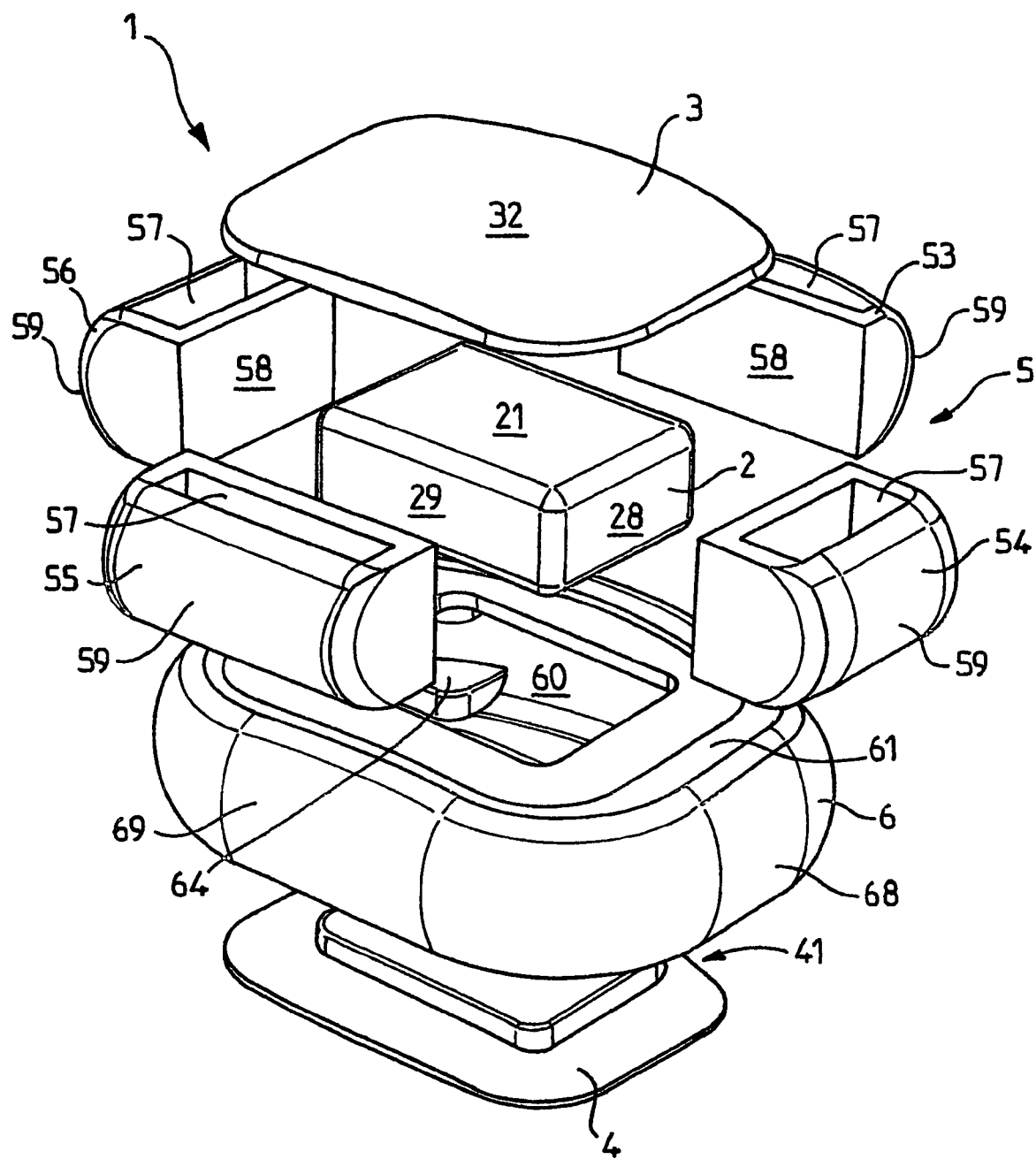
FIG. 16 shows an exploded view of a variant of the invention in which the core has a straight parallelepiped shape and in which the inner casing consists of four separate arms.
Figure 17:
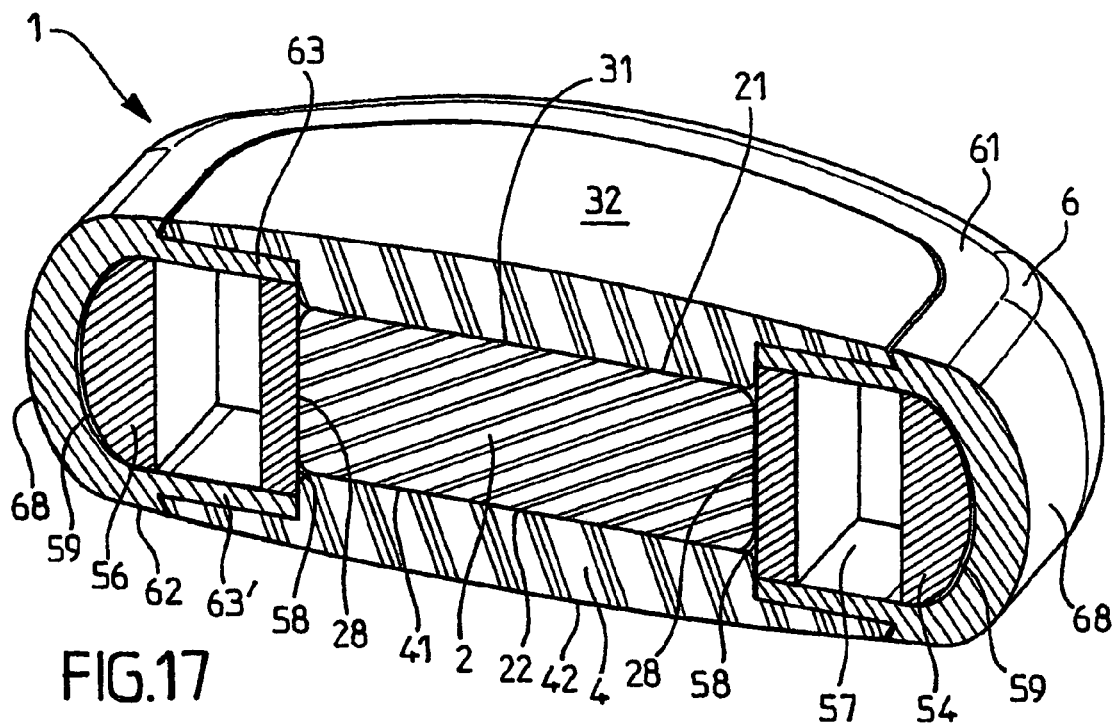
FIG. 17 is a view in vertical section and in perspective of the variant of FIG. 16 in the assembled state.
Figure 18:
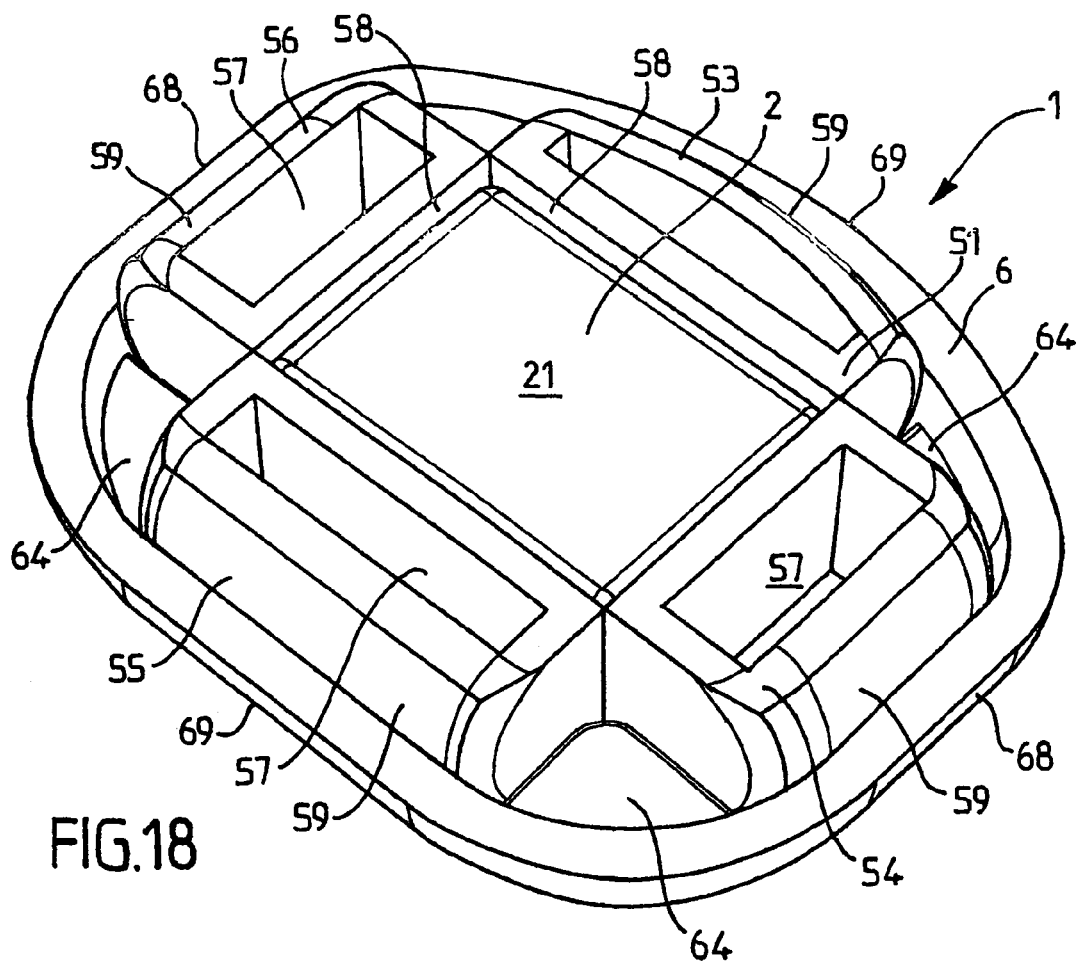
FIG. 18 is a view in partial horizontal section and in perspective of the variant of FIG. 16 in the assembled state.

In a variant shown in FIGS. 14 and 15, the upper plate (3) or the lower plate (4), and preferably both the upper plate (3) and lower plate (4), has/have an annular cavity (35, 45) adjacent to the outer face (32, 42).

This annular cavity (35, 45), which is substantially rectangular, is designed to cooperate with the centripetal flange (63, 63') of the outer casing (6).

In a variant shown in FIGS. 16 to 19, the core (2) has a substantially straight parallelepiped shape. The upper wall (21) and lower wall (22) are therefore substantially horizontal and do not exhibit any curvature; however, the edges of the walls are nevertheless rounded.

In this variant, the core (2) is more flexible than in the basic version.

Figure 19:
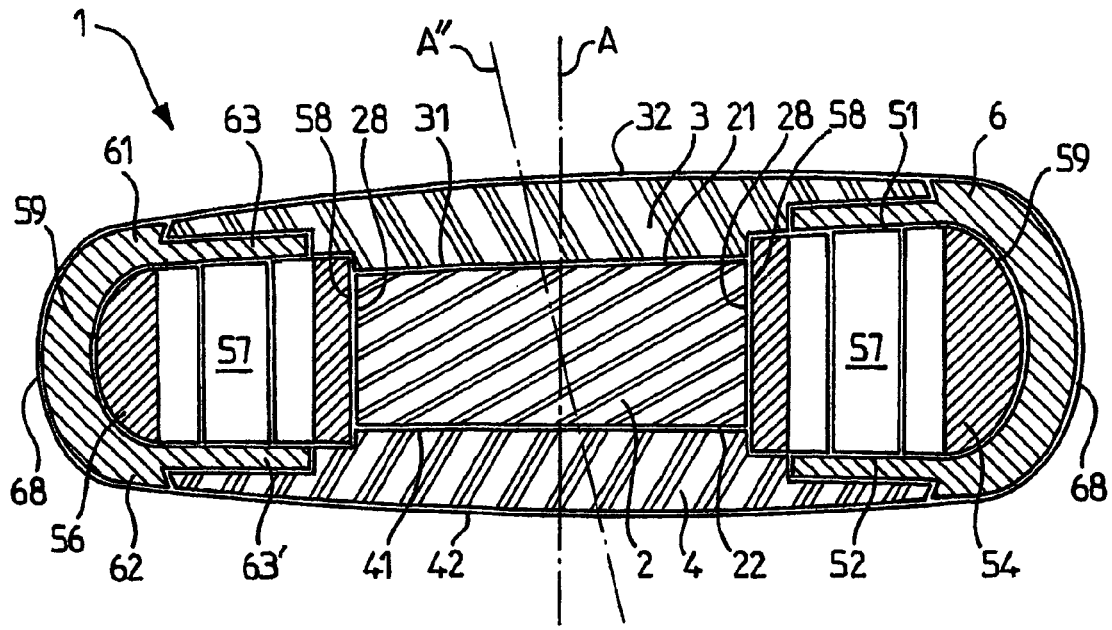
FIG. 19 shows a view in vertical section of the variant of FIG. 16 during a flexural movement.
Figure 21:
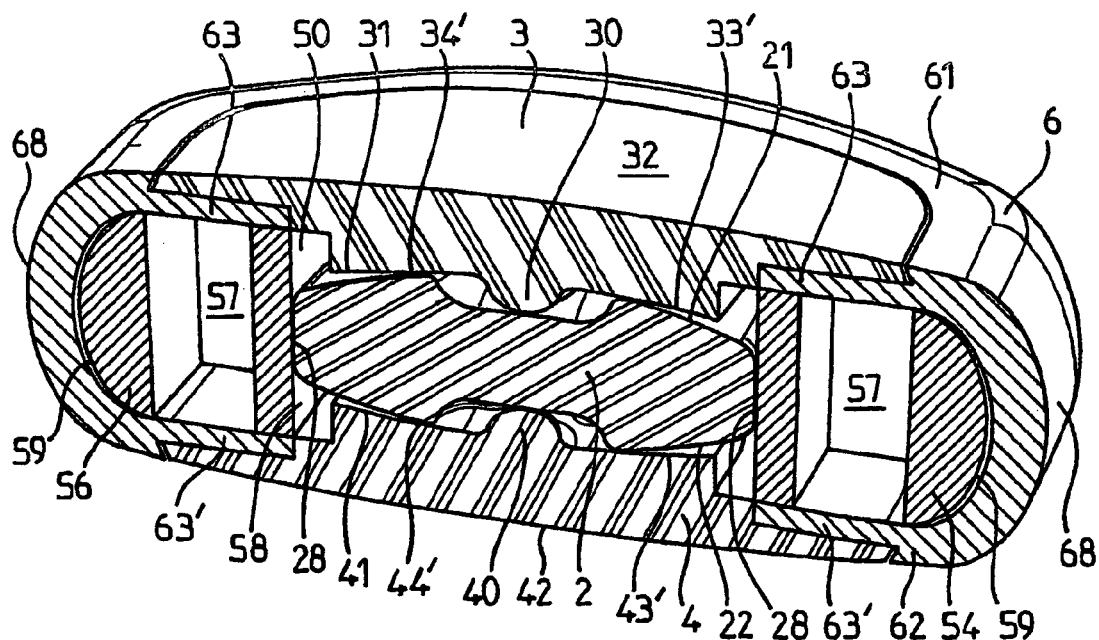
FIG. 21 is a view in vertical section and in perspective of the variant of FIG. 20 in the assembled state.

In this variant, the overall flexibility of the prosthesis is less than that of the prosthesis according to the basic version. This is because, during forward flexion, as shown in FIG. 19, there is no significant displacement of the core (2) in the inner casing (5), as is the case in the basic version (cf. FIG. 12). The mean axis of the column A which has passed from the vertical position to the forward-inclined position A" has undergone essentially only a rotation with respect to the vertical.

In a variant shown in FIGS. 20 to 25, at least one inner face (31, 41) respectively of said upper plate (3) and/or lower plate (4) has a projection (30, 40) which is formed for example by a hemisphere positioned in the centre of the bottom surface (38, 48) of the inner face (31, 41) of the plate and oriented toward the inside of the prosthesis.

It should be noted that this variant is compatible with the following two variants: the variant in which the inner faces of the plates are flat and the variant in which the outer centrifugal edges of the inner faces of the plates are raised toward the core (2).

Moreover, in this variant, said core (2) comprises, respectively on its upper face (21) and/or lower face (22), two grooves (23/23', 24/24') which are oriented in two perpendicular directions and are designed to cooperate respectively with the projection (30, 40). These grooves have in cross section a semicircular shape with a radius which is essentially identical to the radius of the hemispherical shape of the projection (30, 40).

Said grooves (23/23', 24/24') are oriented in the same directions as the favored directions of flexibility of the inner casing (5), that is to say on the one hand in the direction of left/right lateral inclination in respect of the grooves (23, 24) and on the other hand in the direction of flexion/extension in respect of the grooves (23', 24').

The length of each groove is adapted as a function of the desired amplitude for each lateral inclination or flexion/extension movement.

The ends of the grooves are rounded with the same radius as the radius of the transverse semicircular shape and the point (25, 26) of intersection respectively of the two grooves (23, 23') on the upper face (21) and of the grooves (24, 24') on the lower face (22) is designed to allow the projection (30, 40) to move in any favored direction formed by the grooves starting from this point of intersection.

Figure 20:
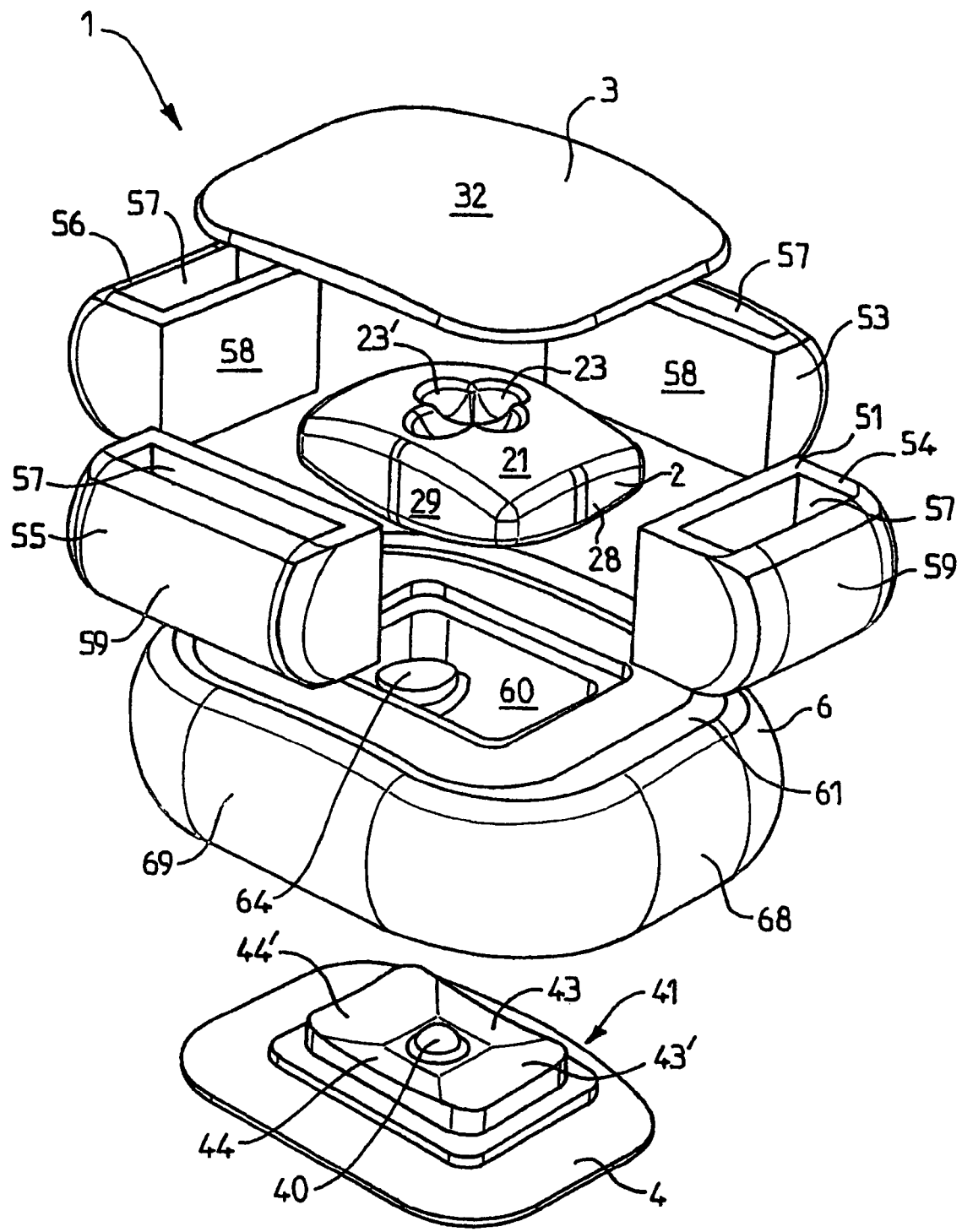
FIG. 20 shows an exploded view of a variant of the invention in which the core has a parallelepiped shape with rounded upper and lower faces and provided with grooves, in which the upper and lower plates are provided with a projection which is designed to cooperate with said grooves and in which the inner casing consists of four separate arms.
Figure 22:
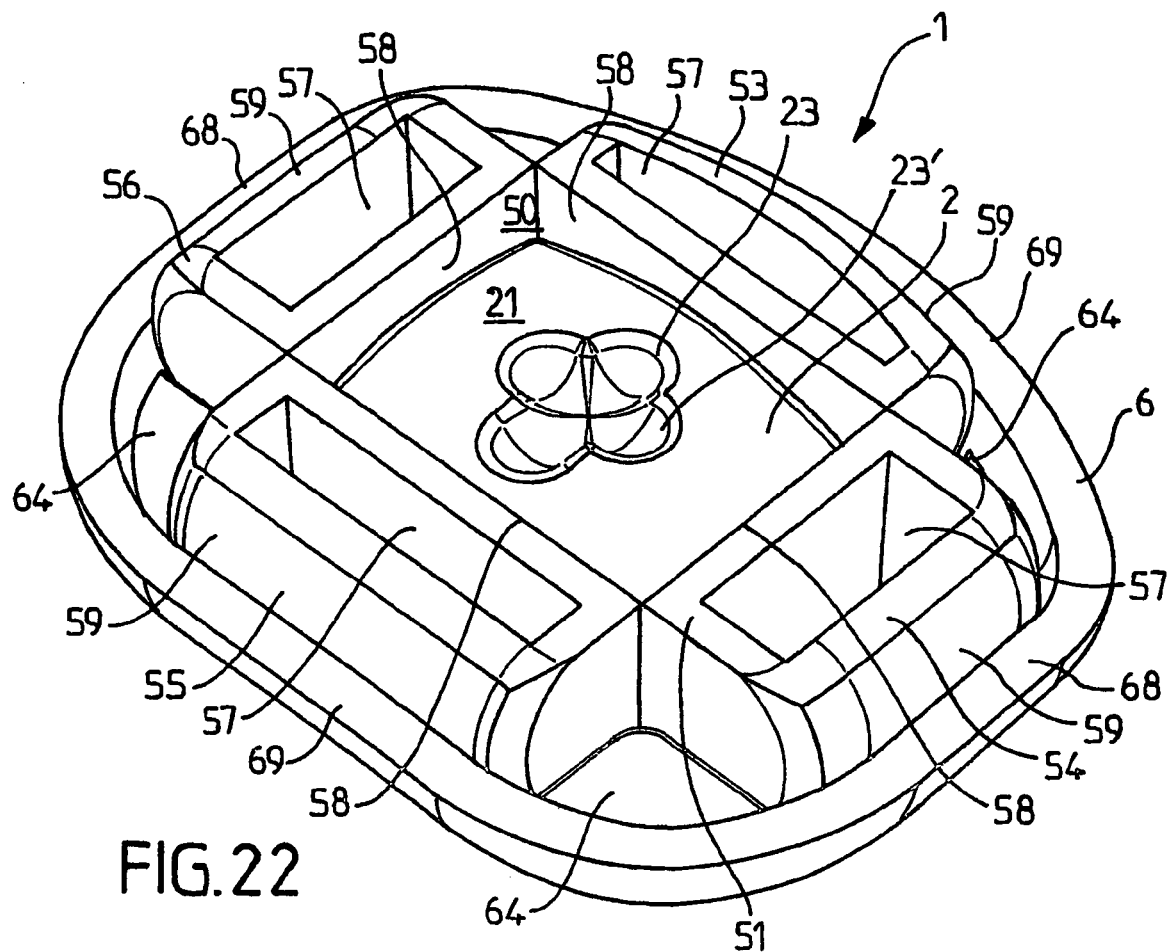
FIG. 22 is a view in partial horizontal section and in perspective of the variant of FIG. 20 in the assembled state.
Figure 23:
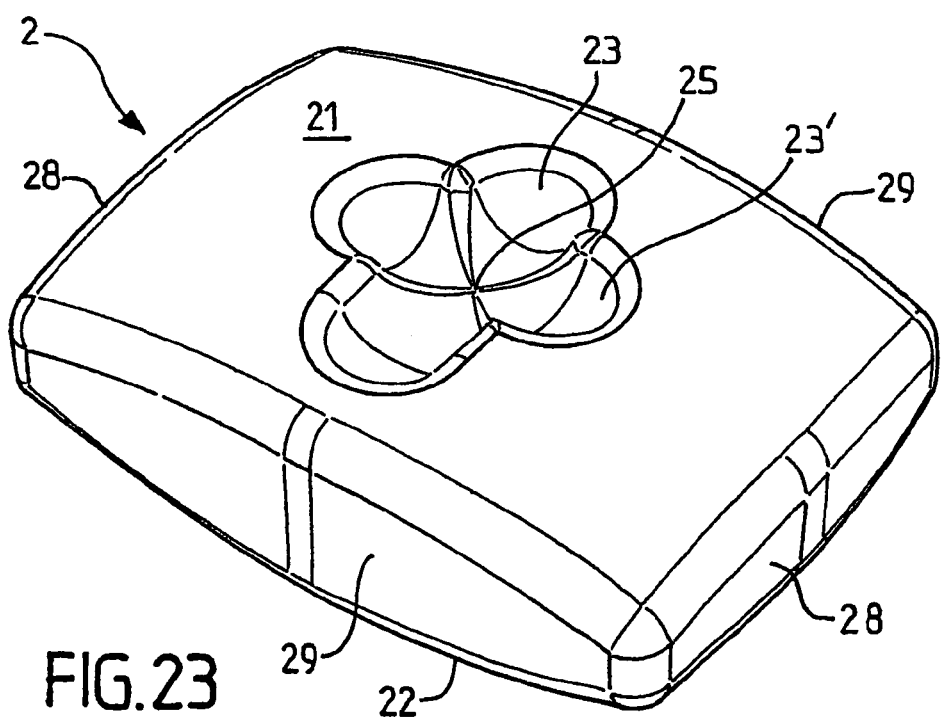
FIG. 23 shows a perspective view of the core of the variant of FIG. 20.
Figure 24:
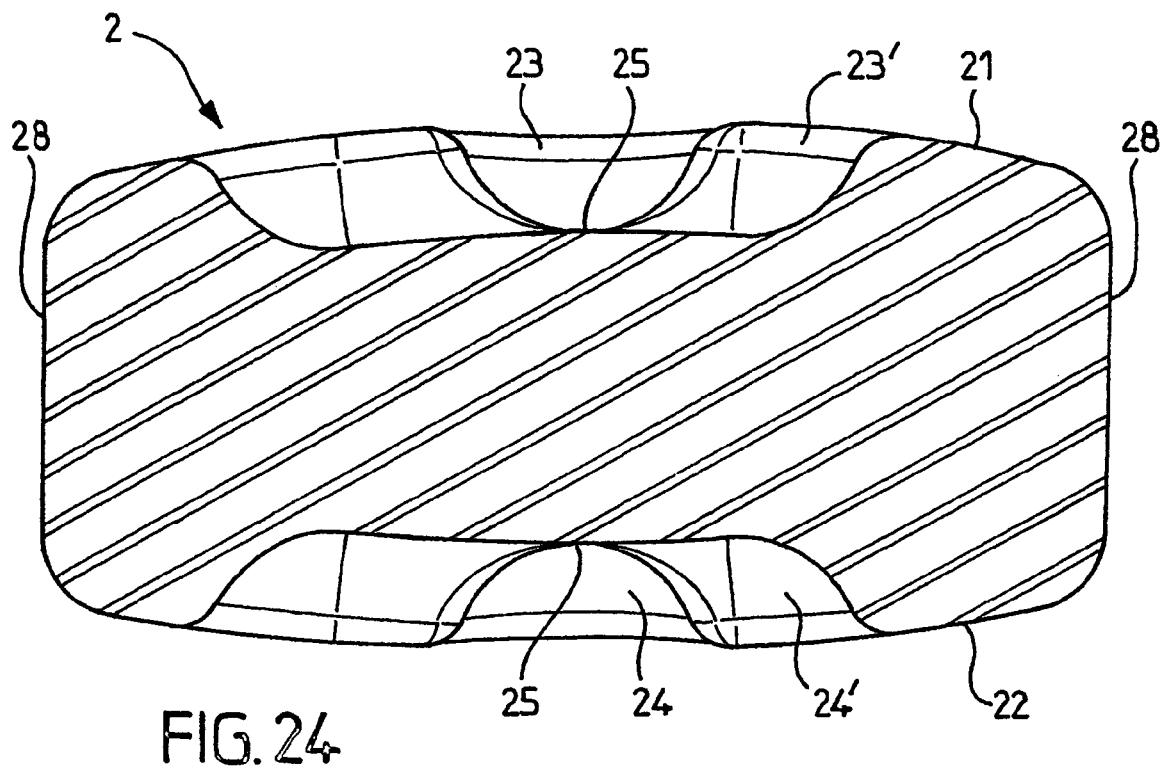
FIG. 24 shows a view in longitudinal section of the core for the variant of FIG. 20.
Figure 25:
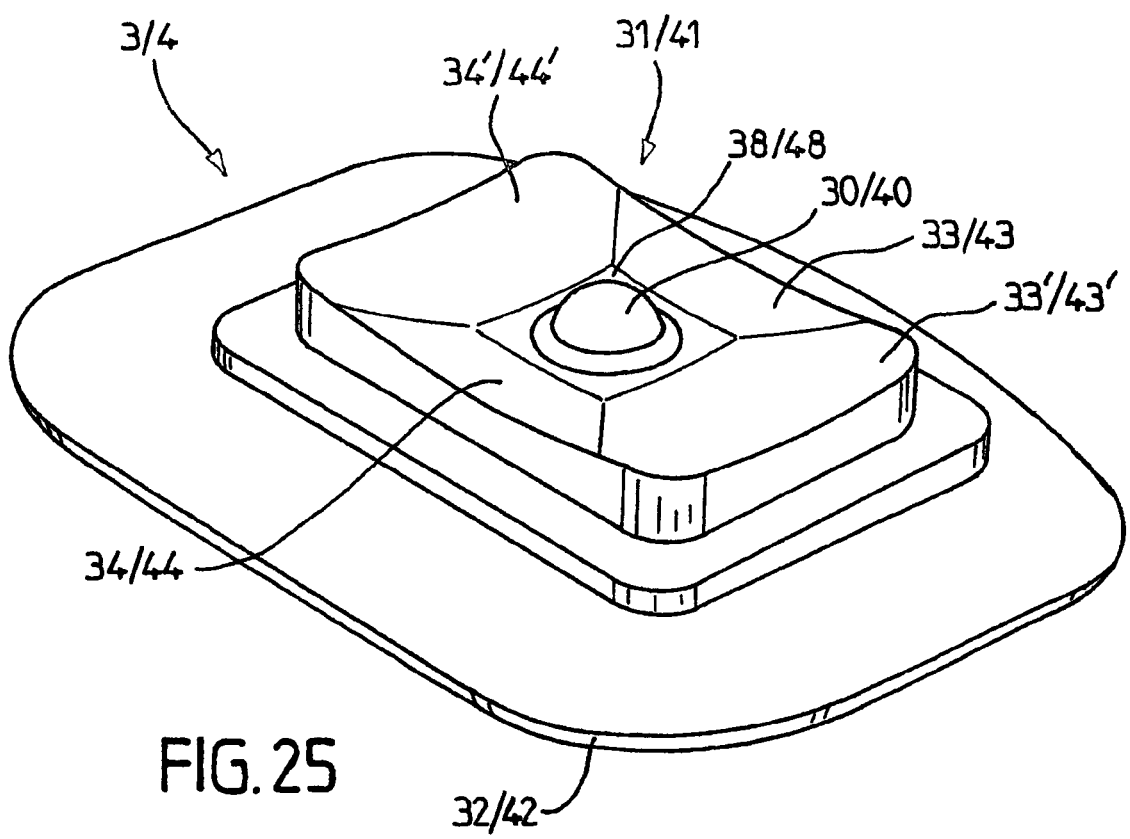
FIG. 25 shows a perspective view of a plate for the variant of FIG. 20.
Figure 26:
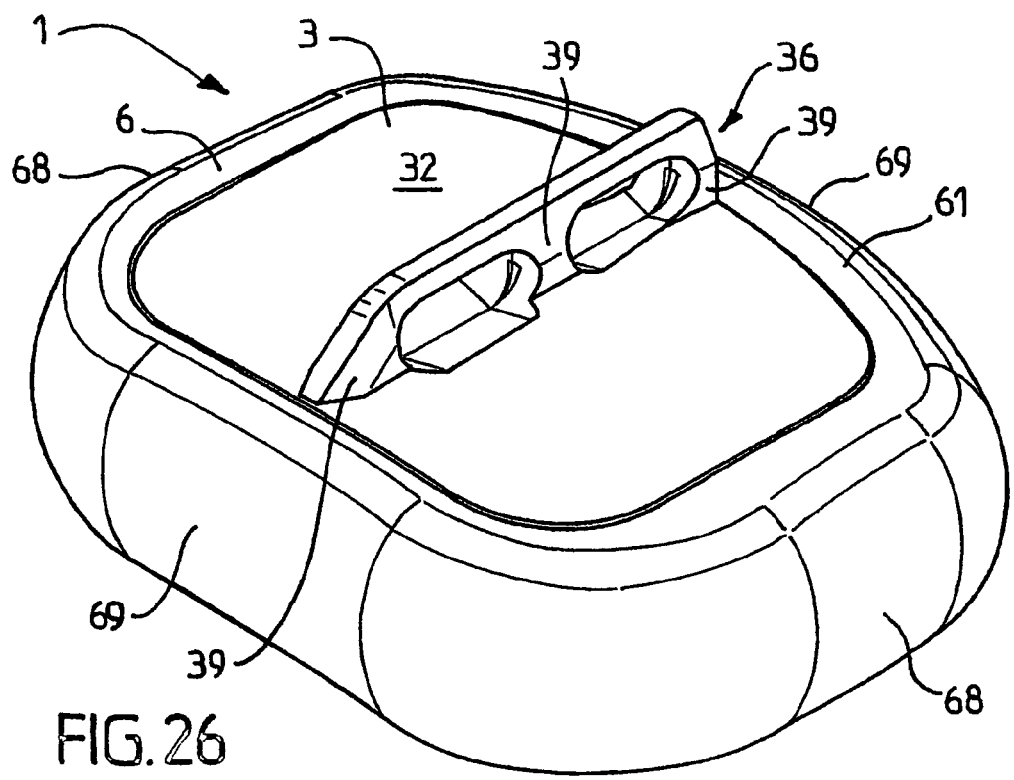
FIG. 26 shows a perspective view of a variant of the invention in which the upper and lower plates are provided with a fixing rail.
Figure 27:
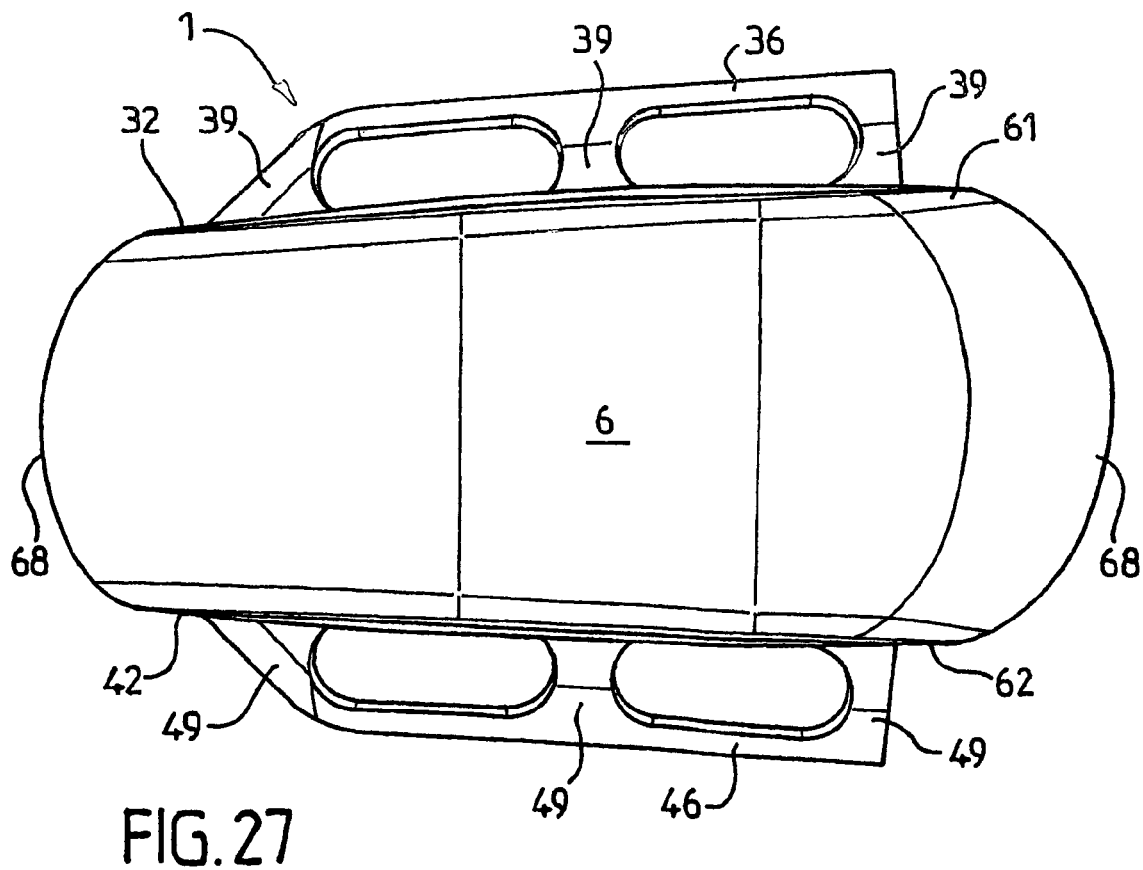
FIG. 27 shows a side view of the variant of FIG. 26.
Figure 28:
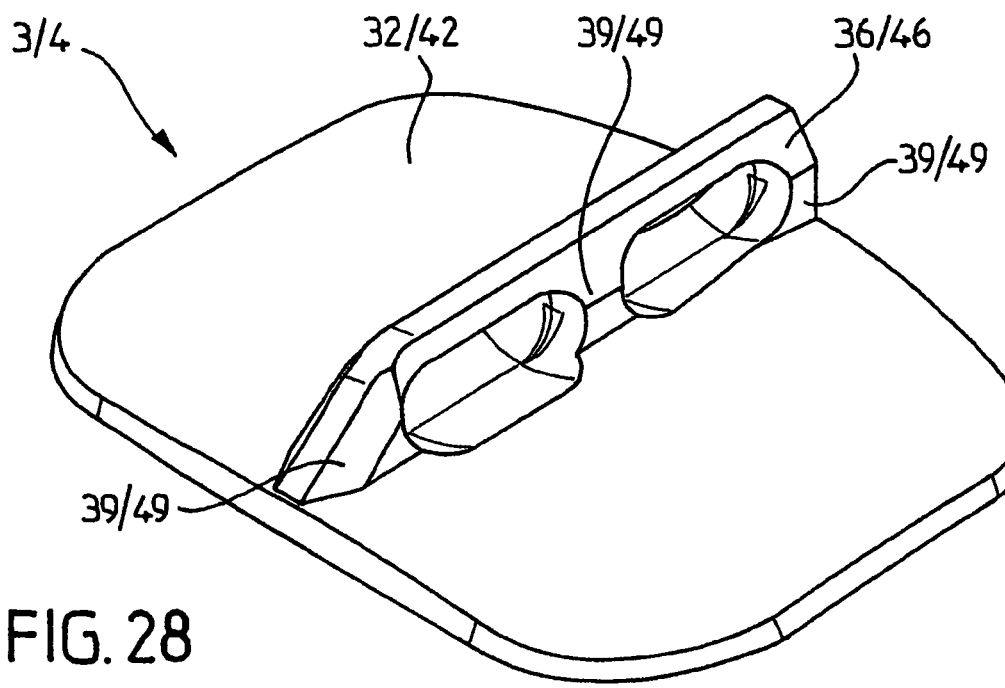
FIG. 28 shows a perspective view of a plate for the variant of FIG. 26.
Figure 29:
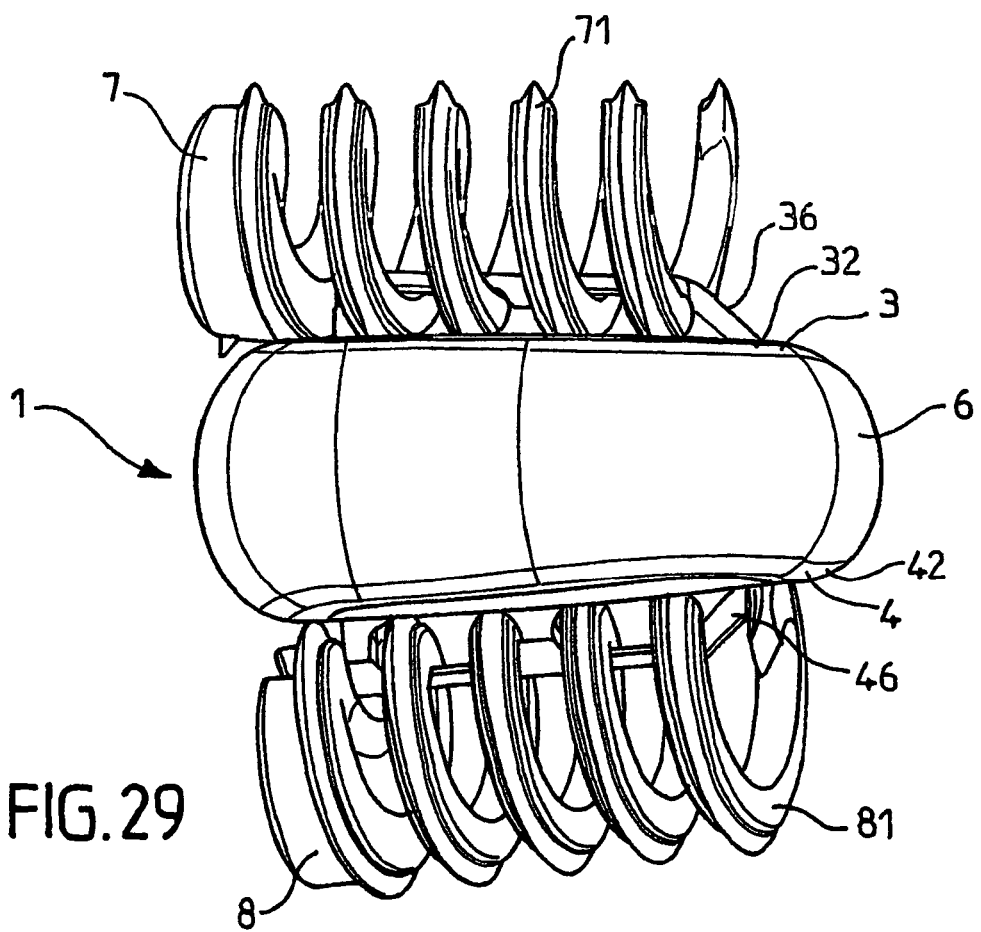
FIG. 29 shows a perspective view of a prosthesis according to the variant of FIG. 26 which is provided with fixing means for fixing it to the vertebrae.
Figure 30:
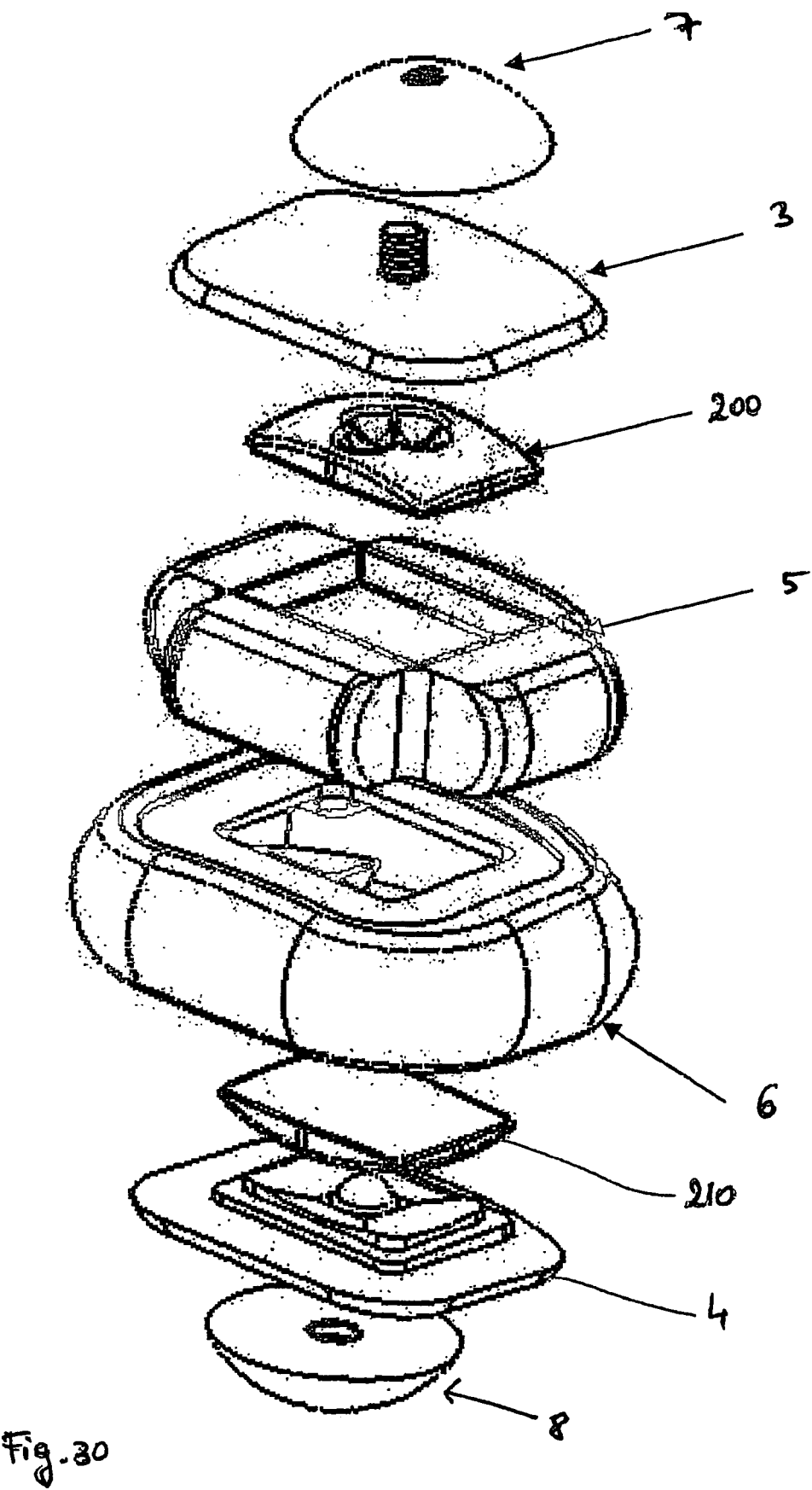
FIG. 30 shows an exploded view of another variant of the intervertebral prosthesis according to the invention.
Figure 31:
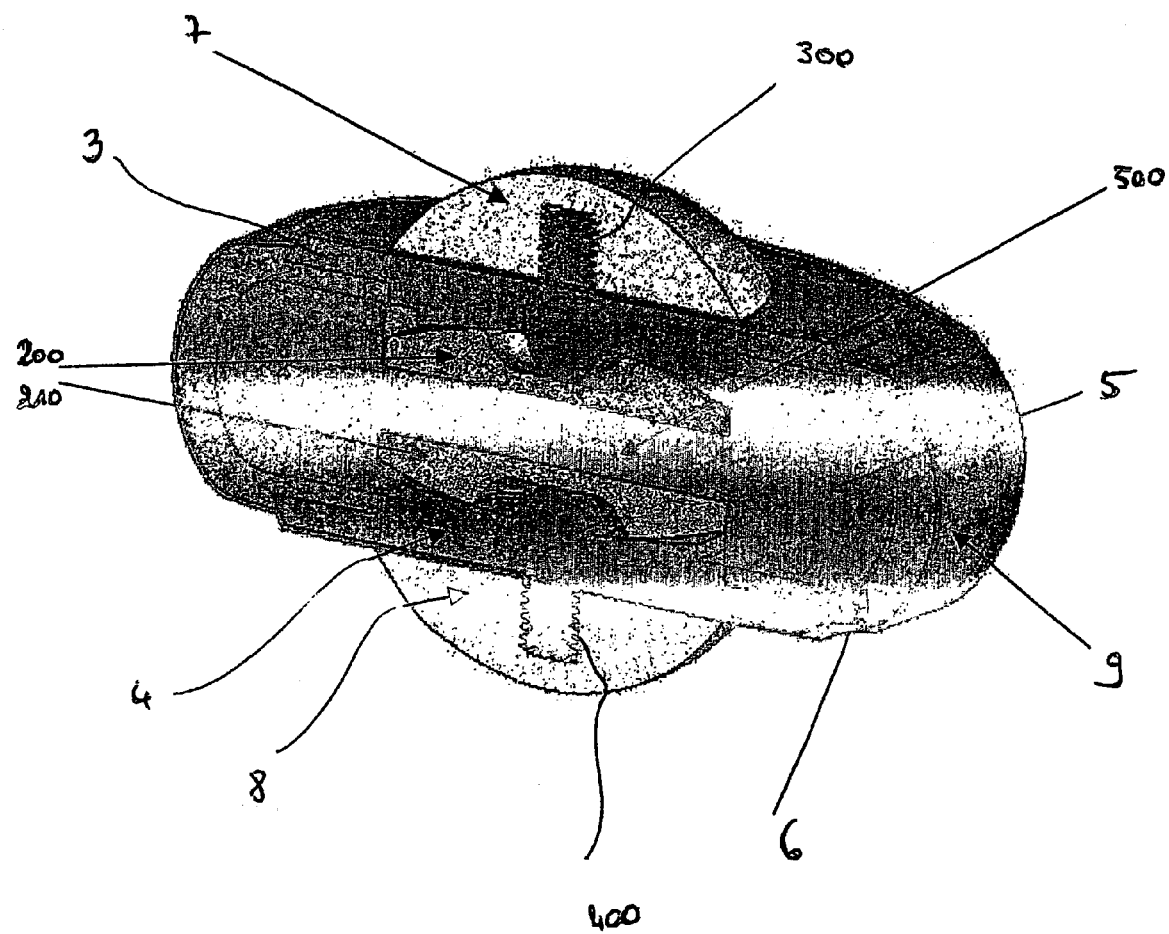
FIG. 31 shows a view in vertical section and in perspective of the prosthesis of FIG. 30 in the assembled state.
Figure 32:
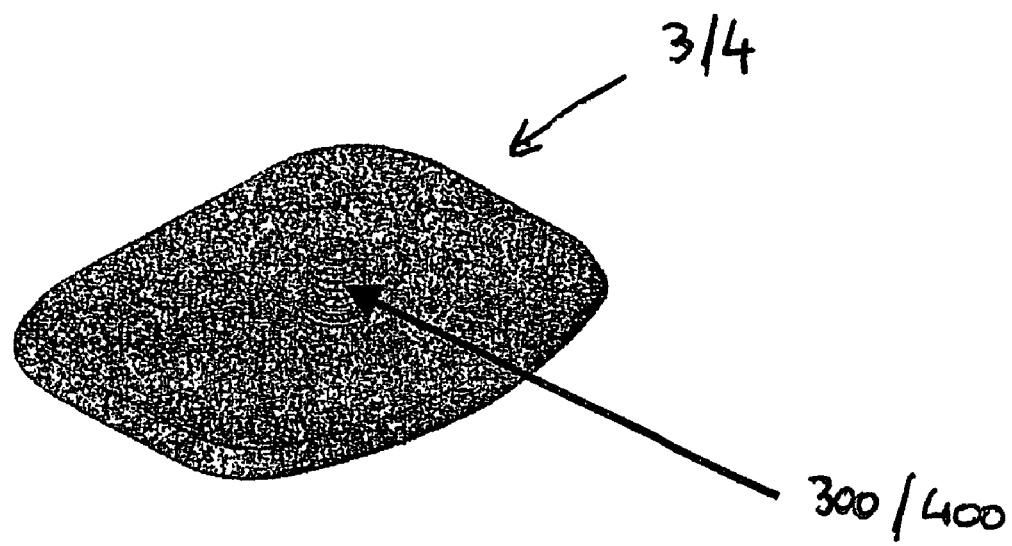
FIG. 32 shows a view from above and in perspective of a plate forming the prosthesis of FIG. 30.
Figure 33:
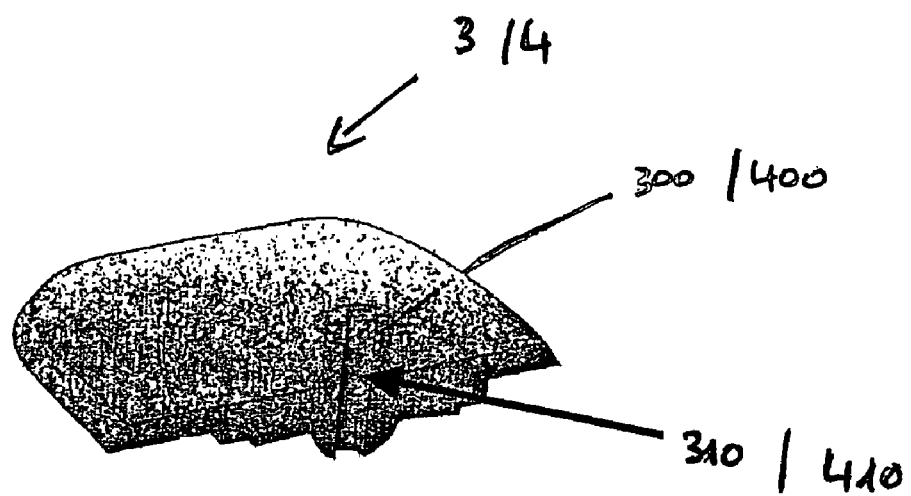
FIG. 33 shows a view in section and in perspective of the plate of FIG. 32.

Also in this variant, the arms (53, 54, 55, 56) each form a whole, that is to say that the inner casing (5) consists of four parts: the four arms, as can be seen in FIG. 20.

The horizontal cross shape of the inner casing (5) is thus maintained by the peripheral outer casing (6).

It is possible that not all the arms have the same flexibility. For example, it is possible to provide a rear arm (54) and a front arm (56) which are more flexible than the left arm (53) and right arm (55). Thus, the flexibility of the prosthesis is greater in terms of flexion/extension movements than in terms of lateral inclination movements.

It is also possible to imagine that the inner casing (5) and the outer casing (6) form a single part, which may optionally have non-uniform intrinsic characteristics.

In a variant shown in FIGS. 26 to 29, said upper plate (3) and/or lower plate (4) has/have a fixing rail (36, 46) on its/their outer face(s) (32, 42).

This fixing rail is oriented substantially in the sagittal flexion/extension direction. It consists of a longitudinal bridge which is connected to the outer face (32, 42) of the plate (3, 4) by at least one pillar (39, 49) and preferably three pillars (39, 49). A clearance is left between each pillar in order to allow the passage of a fixing means (7, 8).

Preferably, each upper (7) and lower (8) fixing means consists of an intersomatic cage of the type disclosed in French patent application No. FR 02/01654, comprising a central hollow space delimited by a helical structure (71, 81) composed of helical turns which are not joined axially and comprising, at one axial end, a gripping means.

The upper (7) and lower (8) fixing means thus make it possible to fix respectively the plates (3, 4) to the overlying and underlying bone walls of the spinal column.

The helical spiral may be inserted by screwing it on the one hand into the vertebrae and on the other hand into the clearances left between the pillars of the rail.

In a variant shown in FIGS. 30 to 33, the intervertebral prosthesis (1) is advantageously formed of two cores (200, 210) having grooves in the shape of crosses so as to confer the anatomical directions.

In this variant, the inner casing (5) has a longitudinal flexible membrane (500) which extends in a median plane so as to form two cavities which are designed to receive respectively said cores (200, 210).

In order to absorb shocks and also axial compression, the membrane (500) of said inner casing (5) is made of a flexible polymer.

The upper and lower plates (3, 4) respectively comprise a through-hole (310, 410). Advantageously, the through-hole (310, 410) is extended by a threaded tubular zone (300, 400) so as to allow a contact element (7, 8) to be screwed onto each of said plates (3, 4). These contact elements (7, 8) are designed to be brought into contact respectively with the overlying and underlying vertebrae.

The opening on either side of the plates (3, 4) thus allows the injection of a fluid into the two cavities of the inner casing (5). Advantageously, the fluid injected into each of the cavities of the inner casing (5) respectively through each of said plates (3, 4) forms the two cores (200, 210) of the intervertebral prosthesis (1).

In order to hold the elements forming the intervertebral prosthesis (1), namely the two cores (200, 210), the inner casing (5), the outer casing (6) and the upper and lower plates (3, 4), while maintaining the shock absorption properties of said intervertebral prosthesis (1), said elements are advantageously overmolded with a flexible elastomer (9) before the contact elements are screwed onto the plates (3, 4).

The invention is described above by way of example. It will be understood that the person skilled in the art may implement different variants of the invention without departing from the scope of the patent.

The invention claimed is:

1. An intervertebral prosthesis comprising:
    at least one non-spherical core positioned between an upper plate and a lower plate,
    said at least one core having a plurality of lateral faces,
    said upper and lower plates respectively comprising inner faces configured for allowing a displacement of said at least one core inside said prosthesis by sliding on the inner faces of said upper and lower plates,
    a flexible inner casing and at least one flexible outer casing, said at least one flexible outer casing containing a cavity in which said inner casing is positioned and said inner casing having a cavity in which said at least one core is positioned so that said at least one core is surrounded on all said lateral faces by said flexible inner casing, and
    said inner casing having in horizontal section a shape of a cross formed by four horizontal arms oriented perpendicularly, the arms so arranged defining two favored directions of flexibility oriented perpendicularly to each other.

2. The intervertebral prosthesis as claimed in claim 1, wherein at least one inner face respectively of said upper plate and lower plate, has means for guiding the displacement of said at least one core.

3. The intervertebral prosthesis as claimed in claim 2, wherein said guiding means are oriented in two perpendicular directions and in the same directions as the favored directions of flexibility of the inner casing.

4. The intervertebral prosthesis as claimed in claim 2, wherein said guiding means consist of inclined surfaces and outer edges of the inclined surfaces are oriented toward the at least one core.

5. The intervertebral prosthesis as claimed in claim 1, wherein at least one of the inner faces respectively of said upper plate and lower plate has a projection and said at least one core comprising, respectively on at least one of an upper face and a lower face, two grooves which are oriented in two perpendicular directions.

6. The intervertebral prosthesis as claimed in claim 5, wherein said grooves are oriented in the same directions as the favored directions of flexibility of the inner casing.

7. The intervertebral prosthesis as claimed in claim 1, wherein at least one of the inner faces respectively of said upper plate and said lower plate, is flat.

8. The intervertebral prosthesis as claimed in claim 1, wherein the inner faces are flat.

9. The intervertebral prosthesis as claimed in claim 1, wherein said at least one non-spherical core has a substantially parallelepiped shape.

10. The intervertebral prosthesis as claimed in claim 1, wherein the upper face and lower face of said at least one core are rounded in the favored directions of flexibility of the inner casing.

11. The intervertebral prosthesis as claimed in claim 1, wherein said at least one non-spherical core has rounded edges.

12. The intervertebral prosthesis as claimed in claim 1, wherein said arms each have a hole which opens onto an upper face and a lower face of said inner casing.

13. The intervertebral prosthesis as claimed in claim 1, wherein centripetal faces of said arms are straight.

14. The intervertebral prosthesis as claimed in claim 1, wherein centrifugal faces of said arms are rounded and centripetal faces of the at least one outer casing are rounded.

15. The intervertebral prosthesis as claimed in claim 1, wherein said at least one outer casing has inner fins which are designed to hold the horizontal arms of the inner casing.

16. The intervertebral prosthesis as claimed in claim 1, wherein the inner casing and the at least one outer casing are made in one piece.

17. The intervertebral prosthesis as claimed in claim 1, wherein said at least one outer casing has cutouts on at least one of an upper wall and a lower wall for the passage of outer faces of the upper plate and lower plate.

18. The intervertebral prosthesis as claimed in claim 17, wherein at least one of said upper plate and said lower plate have an annular cavity adjacent to at least one of the outer faces and at least one of said upper wall and said lower wall has a centripetal flange which is designed to cooperate with said annular cavity.

19. The intervertebral prosthesis as claimed in claim 1, wherein at least one of said upper plate and said lower plate is flexible.

20. The intervertebral prosthesis as claimed in claim 1, wherein at least one of said upper plate and said lower plate has a fixing rail on at least one outer face.

21. The intervertebral prosthesis as claimed in claim 1, further comprising means for fixing at least one of the upper plate and the lower plate.

22. The intervertebral prosthesis as claimed in claim 1, wherein said prosthesis is formed of two cores.

23. The intervertebral prosthesis as claimed in claim 22, wherein the inner casing has a longitudinal median membrane which separates the two cores.

24. The intervertebral prosthesis as claimed in claim 23, wherein the membrane of said inner casing is flexible.

25. The intervertebral prosthesis as claimed in claim 1, wherein at least one of the plates comprises a through-hole to allow the passage of a fluid into said inner casing.

26. The intervertebral prosthesis as claimed in claim 25, wherein the through-hole is extended by a threaded tubular zone which is designed to cooperate with a complementary threaded zone of a contact element which is designed to be brought into contact with one of the vertebrae.

27. The intervertebral prosthesis as claimed in claim 1, wherein said prosthesis of said at least one core, the inner casing, the outer casing and the plates is overmolded with a flexible elastomer.

28. The intervertebral prosthesis as claimed in claim 1, wherein said at least one core is solid.

29. The intervertebral prosthesis as claimed in claim 1, wherein said at least one core is liquid.

* * * * *